US008956160B2

(12) United States Patent
Willison et al.

(10) Patent No.: US 8,956,160 B2
(45) Date of Patent: Feb. 17, 2015

(54) DEVICE AND METHOD FOR DELIVERING AN ORAL CARE AGENT

(75) Inventors: Michael P. Willison, Rockford, MI (US); Joseph C. Townshend, Grand Rapids, MI (US); Christopher D. Bryan, Morristown, NJ (US); Emilie S. Beskar, Norristown, PA (US); Sreenivasu Mudumba, Union City, CA (US); Adrian Faasse, Carmel Valley, CA (US); Janet Lai, Palo Alto, CA (US)

(73) Assignee: Ranir, LLC, Grand Rapids, MI (US)

( * ) Notice: Subject to any disclaimer, the term of this patent is extended or adjusted under 35 U.S.C. 154(b) by 2046 days.

(21) Appl. No.: 10/187,666

(22) Filed: Jul. 2, 2002

(65) Prior Publication Data

US 2004/0005277 A1 Jan. 8, 2004

(51) Int. Cl.
| | |
|---|---|
| *A61Q 11/00* | (2006.01) |
| *A61C 5/00* | (2006.01) |
| *A61K 6/00* | (2006.01) |
| *A61K 8/00* | (2006.01) |
| *A61K 8/22* | (2006.01) |
| *A61C 19/06* | (2006.01) |
| *A61C 19/08* | (2006.01) |

(52) U.S. Cl.
CPC . *A61K 8/22* (2013.01); *A61C 19/06* (2013.01); *A61C 19/063* (2013.01); *A61C 19/066* (2013.01); *A61C 19/08* (2013.01); *A61Q 11/00* (2013.01)
USPC .......... 433/215; 433/216; 433/217.1; 424/49; 424/53; 424/401

(58) Field of Classification Search
USPC ............ 424/49, 53, 401; 433/216, 215, 217.1
See application file for complete search history.

(56) References Cited

U.S. PATENT DOCUMENTS

| | | | | |
|---|---|---|---|---|
| 3,416,527 | A | 12/1968 | Hoef | 128/260 |
| 3,527,219 | A | 9/1970 | Greenberg | 128/260 |
| 4,173,219 | A * | 11/1979 | Lentine | 604/77 |
| 4,581,821 | A | 4/1986 | Cahalan et al. | 29/877 |
| 4,615,697 | A | 10/1986 | Robinson | 604/890 |
| 4,713,243 | A | 12/1987 | Schiraldi et al. | 424/151 |
| 4,772,470 | A | 9/1988 | Inoue et al. | 424/435 |
| RE33,093 | E | 10/1989 | Schiraldi et al. | 424/676 |
| 5,098,303 | A | 3/1992 | Fischer | 433/215 |
| 5,279,816 | A | 1/1994 | Church et al. | 424/53 |
| 5,326,685 | A * | 7/1994 | Gaglio et al. | 433/215 |
| 5,438,076 | A | 8/1995 | Friedman et al. | 514/772.6 |
| 5,575,654 | A | 11/1996 | Fontenot | 433/215 |
| 5,599,553 | A | 2/1997 | Chung | 424/435 |
| 5,614,223 | A | 3/1997 | Sipos | 424/489 |
| 5,626,866 | A | 5/1997 | Ebert et al. | 424/447 |
| 5,643,603 | A | 7/1997 | Bottenberg et al. | 424/488 |
| 5,648,399 | A | 7/1997 | Friedman et al. | 514/772.6 |
| 5,700,478 | A | 12/1997 | Biegajski et al. | 424/434 |
| 5,780,045 | A * | 7/1998 | McQuinn et al. | 424/434 |
| 5,851,512 | A | 12/1998 | Fischer | 424/49 |
| 5,863,202 | A | 1/1999 | Fontenot et al. | 433/215 |
| 5,879,691 | A | 3/1999 | Sagel et al. | 429/401 |
| 5,891,453 | A | 4/1999 | Sagel et al. | 424/401 |
| 5,894,017 | A | 4/1999 | Sagel et al. | 424/401 |
| 5,928,628 | A | 7/1999 | Pellico | 424/49 |
| 5,961,958 | A | 10/1999 | Homola et al. | 424/49 |
| 5,980,249 | A | 11/1999 | Fontenot | 433/80 |
| 5,985,249 | A | 11/1999 | Fischer | 424/49 |
| 5,989,569 | A * | 11/1999 | Dirksing et al. | 424/401 |
| 6,004,538 | A * | 12/1999 | Hughes et al. | 424/49 |
| 6,004,582 | A * | 12/1999 | Faour et al. | 424/473 |
| 6,036,943 | A | 3/2000 | Fischer | 424/49 |
| 6,045,811 | A | 4/2000 | Dirksing et al. | 424/401 |
| 6,074,719 | A * | 6/2000 | Fukushi et al. | 428/36.9 |
| 6,096,328 | A | 8/2000 | Sagel et al. | 424/401 |
| 6,136,297 | A | 10/2000 | Sagel et al. | 424/49 |
| 6,197,331 | B1 | 3/2001 | Lerner et al. | 424/448 |

(Continued)

FOREIGN PATENT DOCUMENTS

| | | | |
|---|---|---|---|
| CA | 2293352 | 12/1998 | ............... A61K 8/72 |
| CA | 2338331 | 2/2000 | ............. A61C 19/06 |

(Continued)

OTHER PUBLICATIONS

D. A. McMillan et al., "Peroxide Degradation Kinetics During Use of Crest Whitestrips™," www.dentalcare.com/soap/products/research/aadr01/pp1101.htm, Sep. 16, 2002.

Xantia™ Advertising Brochure, Manufactured by: Dexcel™ Pharma Technologies, Ltd. Jerusalem, Isreal, Dist. by: Dexcel™ Pharma, Inc., Edison, NJ 08837 (date unknown).

Crest Whitestrips™ Advertising Brochure, Dist. By: Colgate-Palmolive Company, New York, NY 10022 (date unknown).

Robert W. Gerlach, DDS et al., "Vital Bleaching with Whitening Strips: Summary of Clinical Research on Effectiveness and Tolerability," *The Journal of Contemporary Dental Practice*, vol. 2, No. 3, Summer Issue, 2001.

(Continued)

*Primary Examiner* — Lezah Roberts
(74) *Attorney, Agent, or Firm* — Warner Norcross & Judd LLP

(57) ABSTRACT

An oral care agent delivery device is provided which comprises a permanently deformable backing layer, an anchor layer overtop the backing layer, and an oral care layer overtop the anchor layer. The device is sized to fit over a plurality of teeth in an upper or lower dental arch of a subject. The oral care layer comprises at least one oral care agent and at least one hydrophilic polymer. The oral care layer is in contact with the anchor layer and forms an adhesive bond with the anchor layer; however, the oral care layer is minimally invested in the anchoring layer. When hydrated, the oral care layer has an adhesiveness relative to the surface of a user's teeth that is sufficient to retain the device on the user's teeth when placed thereon. The device can also have an oral care agent which is activated on hydration of the oral care layer, or an oral care layer which releases the oral care agent over time.

157 Claims, 4 Drawing Sheets

(56) References Cited

U.S. PATENT DOCUMENTS

| | | | |
|---|---|---|---|
| 6,247,930 B1 * | 6/2001 | Chiang et al. | 433/80 |
| 6,274,122 B1 | 8/2001 | McLaughlin | 424/53 |
| 6,312,671 B1 | 11/2001 | Jensen et al. | 424/53 |
| 6,325,993 B1 | 12/2001 | Saito et al. | 424/49 |
| 6,331,292 B1 | 12/2001 | Montgomery | 424/53 |
| 6,343,932 B1 * | 2/2002 | Wiesel | 433/215 |
| 6,350,438 B1 * | 2/2002 | Witt et al. | 424/53 |
| 6,419,906 B1 | 7/2002 | Xu et al. | 424/53 |
| 6,500,408 B2 | 12/2002 | Chen | 424/53 |
| 6,503,486 B2 | 1/2003 | Xu et al. | 424/53 |
| 6,506,053 B2 | 1/2003 | Wiesel | 433/215 |
| 6,551,579 B2 * | 4/2003 | Sagel et al. | 424/53 |
| 6,582,708 B1 | 6/2003 | Sagel et al. | 424/401 |
| 6,790,460 B2 * | 9/2004 | Shefer et al. | 424/489 |
| 6,905,672 B2 * | 6/2005 | Rajaiah et al. | 424/49 |
| 2001/0024657 A1 | 9/2001 | Lerner et al. | 424/448 |
| 2001/0053375 A1 | 12/2001 | Sagel et al. | 424/401 |
| 2002/0006387 A1 | 1/2002 | Sagel et al. | 424/53 |
| 2002/0006388 A1 | 1/2002 | Sagel et al. | 424/53 |
| 2002/0012685 A1 | 1/2002 | Sagel et al. | 424/401 |
| 2002/0018754 A1 | 2/2002 | Sagel et al. | 424/49 |
| 2002/0037977 A1 | 3/2002 | Feldstein et al. | 526/60 |
| 2002/0103285 A1 * | 8/2002 | Jordan et al. | 524/451 |
| 2002/0146666 A1 | 10/2002 | Sagel et al. | 433/215 |
| 2003/0003421 A1 | 1/2003 | Bestenheider et al. | 433/215 |
| 2003/0059381 A1 | 3/2003 | Goodhart et al. | 424/53 |
| 2003/0133884 A1 | 7/2003 | Chang et al. | 424/53 |
| 2003/0152528 A1 | 8/2003 | Singh et al. | 424/53 |
| 2003/0170308 A1 * | 9/2003 | Cleary et al. | 424/486 |
| 2003/0219389 A1 | 11/2003 | Sagel et al. | 424/53 |

FOREIGN PATENT DOCUMENTS

| | | | |
|---|---|---|---|
| CA | 2424055 | 4/2002 | A61K 9/00 |
| WO | 01/01958 | 1/2001 | A61K 9/00 |
| WO | WO 0168045 | 9/2001 | |
| WO | 02/00182 | 1/2002 | A61K 7/20 |
| WO | 02/071968 | 9/2002 | |
| WO | 03/015656 | 2/2003 | A61C 19/06 |

OTHER PUBLICATIONS

D. A. McMillan et al., "Impact of Increasing Hydrogen Peroxide Concentration on Bleaching Strip Efficacy and Tolerability," *30th Annual Meeting of the AADR*, Mar. 7-10, 2001.

M. P. Harris et al., "Effect of Carbamide Peroxide Concentration on Bleaching Efficacy," *30th Annual Meeting of the AADR*, Mar. 7-10, 2001.

R. W. Gerlach et al., "Use of Peroxide Containing Polyethylene Strips: Effect of Dosing Duration on Initial and Sustained Shade Change," *30th Annual Meeting of the AADR*, Mar. 7-10, 2001.

P. A. Sagel et al., "Clinical Comparison of Whitening with 6.0% and 5.3% Hydrogen Peroxide Whitening Strips," www.dentalcare.com/soap/journals/pgresrch/posters/iadr02/pp1951.htm, Sep. 17, 2002.

D. A. McMillan et al., "Peroxide Degradation Kinetics During Use of Crest Whitestrips™," www.dentalcare.com/soap/products/research/aadr01/pp1101.htm, Sep. 16, 2002.

J. A. Fitzgerald et al., "Comparative In Vitro Antimicrobial Activity of Peroxide Gels in Strip or Tray Bleaching Systems," *30th Annual Meeting of the AADR*, Mar. 7-10, 2001.

Paul A. Sagel, BSChE et al., "Vital Tooth Whitening With a Novel Hydrogen Peroxide Strip System: Design, Kinetics, and Clinical Response," *Compendium*, Supp. No. 29, vol. 21, 2000.

Paul A. Sagel, BSChE et al., "Overview of a Professional Tooth-Whitening System Containing 6.5% Hydrogen Peroxide Whitening Strips," *Compendium*, vol. 23, No. 1A, 2002.

\* cited by examiner

DEVICE AND METHOD FOR DELIVERING AN ORAL CARE AGENT

FIELD OF THE INVENTION

This invention relates to the field of delivering an oral care agent, especially a tooth whitening agent, with a dental device.

BACKGROUND OF THE INVENTION

A variety of devices and methods have been developed to deliver a therapeutic or cosmetic agent to surfaces in the oral cavity. In particular, many systems which deliver a whitening agent to the teeth are available.

A person desiring whiter teeth can choose from professional whitening systems, or can purchase an over-the-counter tooth whitening device for use in the home. In the professional teeth bleaching market, dentists have traditionally used devices for delivery of home bleaching agents which are rigid and custom-fitted to an individual patient's dental arches. One type of delivery device is molded to closely fit a patient's dental arches. Another type of device is an "oversized" rigid custom dental appliance, which is formed by augmenting the facial surfaces of the teeth on stone models made from the patients' teeth, for example with linings such as die spacers or light-cured acrylics. A third type of device is a rigid, bilaminated custom-made dental appliance fabricated from materials ranging from soft porous foams to rigid, non-porous films. The non-porous, rigid thermoplastic shells of such bilaminated dental appliances may encase and support an internal layer of soft, porous foam which absorbs the bleaching agent.

After the custom appliance is fabricated, the dentist typically delivers the first bleaching treatment in the office, and instructs the patient on the proper procedure to dispense bleaching agent in the custom appliance at home. A sufficient amount of bleaching gel is provided so that the patient can perform the prescribed home bleaching regimen. The patient subsequently applies the bleaching agent daily (or as otherwise instructed) by dispensing the bleaching agent into the rigid custom dental appliance and placing the appliance over the dental arch for a specified period of time. At the end of a given treatment period, the dental appliance is removed, thoroughly cleaned to remove any remaining bleaching agent, and stored until the next application. The professional tooth whitening systems generally use a higher concentration of bleaching agent, and consequently the overall treatment period is shorter than that recommended for over-the-counter systems.

However, the rigid, custom-fabricated dental appliances used in professional tooth whitening systems require time-consuming and expensive office visits, laboratory tests and the fitting of each patient's dentition. Furthermore, any changes in the surface of the patient's teeth (such as fillings, crowns, and other accidental or therapeutic alterations of the dentition) affect the fit of the rigid custom dental appliance, and may warrant repeating the entire fabrication procedure. Refabrication of the appliance may also be required in the event of subsequent rebleaching treatments.

Moreover, patients who are inexperienced and unaware of the importance of precision often dispense an improper amount of bleaching agent into the appliance. Dispensing too little bleaching agent into the device results in a less efficacious treatment regimen. Dispensing an excessive amount of bleaching agent into the appliance can cause the agent to be displaced from the appliance into the oral cavity when the device is placed on the teeth, where the agent can be ingested. In addition to such displacement, the bleaching agent can spill or leak from these appliances into the oral cavity, and can cause an unpleasant taste sensation. Ingestion of the bleaching agent may also cause gingival irritation, burning, edema, nausea or allergic reactions. The risk of these more serious side effects increases with the number of treatments, and becomes most significant after the multiple treatments typically required to attain acceptable clinical results. Patients who self-administer bleaching or other medicinal agents may also fail to provide the careful maintenance, cleaning, and storage necessary to ensure that the rigid custom dental appliance performs adequately throughout its entire service life.

There are additional drawbacks with custom bilaminated dental appliances, including occlusion and retention of bleaching agent. Furthermore, cleaning and maintenance of foam-lined dental appliances may be problematic, due to the high surface area and pore volume of the foam materials typically used in such appliances.

Oversized rigid custom dental appliances also have additional drawbacks, including occlusions in the augmented region, increased appliance fabrication time and cost, irritation from the lip of the appliance contacting the gingival region, and decreased retention of the bleaching agent within the target area.

In order to avoid the high cost and inconvenience of professional tooth whitening systems, one may purchase non-professional, "over-the-counter" tooth whitening systems. Some versions of the over-the-counter systems contain a generic "one size fits all" appliance and a container of bleaching gel to be dispensed into the appliance, for example as described in U.S. Pat. No. 3,416,527 of Greenberg and U.S. Pat. No. 3,527,219 of Hoef. However, such generic appliances often have a greater void between the interior walls of the appliance and the teeth as compared to most professionally fitted appliances. Hence, in order to insure intimate contact of the bleaching agent and the teeth surfaces, more bleaching agent is required. Furthermore, the poorer fit of the generic device means a greater loss of bleaching gel into the oral cavity, with the attendant problems described above for the professional tooth whitening appliances. Thus, the leakage problems of professional tooth whitening systems are exacerbated by over-the-counter systems in which the user dispenses the whitening agent into the device. The generic over-the-counter devices also tend to be bulky and uncomfortable in the mouth.

Over-the-counter systems with pre-dispensed bleaching agent are also available. The bleaching agents used in such over-the-counter systems are either viscous liquids or gels containing peroxide compounds. The peroxide compounds are typically provided in hydrated (i.e., active) form, or the peroxide compounds become hydrated due to moisture in the agent or the surrounding air. A typical bleaching agent is a carbamide peroxide gel, in which hydrogen peroxide is coupled to urea in either an anhydrous glycerin base or a soluble, aqueous carboxylic acid polymer base. Upon hydration, the carbamide peroxide breaks down into urea and active peroxide. The active peroxide subsequently breaks down into water and oxygen. Over time, the inherent instability of hydrated peroxide bleaching agents reduces the efficacy of tooth whitening systems with pre-dispensed bleaching agents. The shelf-life of such systems is therefore limited.

U.S. Pat. No. 5,310,563 of Curtis et al. discloses an over-the-counter tooth whitening device in which a putty-like material encapsulating the bleaching agent is molded around the teeth. The putty is held in place by mechanical engagement with undercut surfaces of the teeth, and by friction. The bleaching agent migrates from the composition to the gums and tooth surfaces, rather than being directly in contact with them, which significantly increases the required wearing time. The putty also tends to slip off the teeth, further reducing the efficacy of this type of system.

U.S. Pat. Nos. 5,575,654 and 5,863,202 of Fontenot disclose an over-the-counter tooth whitening system containing prepackaged moldable dental appliance that can be adapted to fit the dental arch, which contains a premeasured amount of medicinal or bleaching agent. It has been observed that the Fontenot device frequently has the problems of bulk and compromised fit. The pressure required to mold the device to the dental arch can also force the bleaching agent out of the device and into the oral cavity.

U.S. Pat. No. 5,980,249 of Fontenot describes a whitening system consisting of a prefabricated, U-shaped dental appliance of hydrophilic foam. The bleaching agent is incorporated or invested in the foam. This device has drawbacks similar to those described above for professional tooth whitening systems using custom bilaminated dental devices. Such drawbacks include occlusion and retention of bleaching agent in the foam, and extrusion of the bleaching agent into the oral cavity upon application of the pressure required to form the device to the user's teeth.

U.S. Pat. Nos. 5,879,691, 5,891,453 and 5,894,017 of Sagel et al. describe over-the-counter tooth whitening systems consisting of flat, flexible strips coated on one surface with an adhesive gel containing a bleaching agent. The strips are meant to be folded over the teeth by the user, with the bleaching agent in contact with, and holding the device onto, the teeth. However, the strip does not adhere well to the tooth surface, and the device tends to slip off the teeth in use.

The bleaching gel is also poorly attached to the Sagel et al. flexible strip, and often adheres to the user's fingers during the manipulations required to fold the strip in place over the dental arch. The potential for contamination of the strip by the user's fingers during routine manipulation is high. Moreover, the bleaching gel can be transferred from the user's fingers to the clothes (which may then be stained or bleached), or to sensitive areas of the body like the eyes, which may cause extreme discomfort. The bleaching gel will also adhere to itself and delaminate from the flexible strip if the user inadvertently folds the strip in upon itself during placement onto the teeth. Such delamination of the bleaching gel reduces the efficacy of the whitening system. Upon removal of the Sagel et al. strip from the teeth, a quantity of the bleaching agent can also adhere to the teeth. This leftover bleaching agent leaves an unpleasant taste in the mouth, and is easily ingested.

Moreover, most of the bleaching gel content of the Sagel et al. strip is delivered and begins to degrade as soon as the strip is placed in the mouth, resulting in reduced efficacy of the whitening system. Repeated and prolonged use of the Sagel et al. strips is thus required to achieve the desired whitening effect.

Over-the-counter whitening systems similar to those described in the Sagel et al. patents are disclosed in U.S. Pat. Nos. 5,989,569 and 6,045,811 of Dirksing et al. The Dirksing et al. system consists of a deformable flat wax strip carrying the same type of bleaching gel as the Sagel et al. strips. Here again, the bleaching gel is poorly adhered to the wax strips, and the Dirksing et al. system likely suffers from the same problems of difficulty of use and reduced efficacy as described above for the Sagel et al. strips.

The known professional and over-the-counter tooth whitening systems can also be used to deliver other oral care agents, such as medicines or antibiotics, to the teeth and gingival tissue. However, the drawbacks described above for the tooth whitening systems are also present when the systems are used to deliver other oral care agents.

What is needed, therefore, is an over-the-counter device for delivering an oral care agent, for example a tooth whitening agent, in which a pre-measured amount of oral care agent is contained within a device that is firmly held onto a user's teeth, and which does not release the oral care agent into the oral cavity in appreciable quantities. The device should also be configured so that the user does not contact the oral care agent during routine manipulation of the device into place over the dental arch. The layer which delivers the oral care agent should also be sufficiently secured to the device so that no residue is left on the user's fingers if the layer inadvertently touched, and no residue is left on the teeth upon removal of the device. Furthermore, the oral care agent should be activated and released from the device over time, so that efficacy of the agent is maximized and the number and duration of each application is reduced.

SUMMARY OF THE INVENTION

It has been found that the deficiencies of both the professional and over-the-counter oral care agent delivery systems discussed above are overcome by the oral care agent delivery device of the invention.

The device of the invention comprises a permanently deformable backing layer, an anchor layer overtop the backing layer, and an oral care layer overtop the anchor layer. The device is sized to fit over a plurality of teeth in an upper or lower dental arch of a subject. The oral care layer comprises at least one oral care agent and at least one hydrophilic polymer. The oral care layer is in contact with the anchor layer and forms an adhesive bond with the anchor layer; however, the oral care layer is minimally invested in the anchoring layer. When hydrated, the oral care layer has an adhesiveness relative to the surface of a user's teeth that is sufficient to retain the device on the user's teeth when placed thereon.

The invention also provides a device which has a substantially non-flat cross section.

The invention also provides a device in which the oral care agent is activated on hydration of the oral care layer.

The invention also provides a device comprising a sustained release oral care layer.

The invention also provides a method for delivering an oral care agent to a plurality of teeth in an upper or lower dental arch in a subject, comprising providing a device which comprises permanently deformable backing layer, an anchor layer overtop the backing layer, and an oral care layer overtop the anchor layer. The device is sized to fit over a plurality of teeth in an upper or lower dental arch of a subject. The oral care layer comprises at least one oral care agent and at least one hydrophilic polymer. The oral care layer is in contact with the anchor layer and forms an adhesive bond with the anchor layer; however, the oral care layer is minimally invested in the anchoring layer. When hydrated, the oral care layer has an adhesiveness relative to the surface of a user's teeth that is sufficient to retain the device on the user's teeth when placed thereon. The oral care agent is delivered by wetting the teeth or the oral care layer, placing the device over the teeth of a dental arch, and conforming the device to the teeth by manual pressure so that the oral care layer is in contact with at least the front surface of the teeth. The device is then left on the teeth for a sufficient time to achieve the desired result whereupon it is removed from the teeth and discarded. The process of delivering the oral care agent can be repeated as necessary.

The invention further provides a method for delivering a tooth whitening agent to a plurality of teeth in an upper or lower dental arch in a subject, comprising providing a device comprising a permanently deformable backing layer, an anchor layer overtop the backing layer, and an oral care layer overtop the anchor layer. The device is sized to fit over a plurality of teeth in an upper or lower dental arch of a subject. The oral care layer comprises at least one tooth whitening agent and at least one hydrophilic polymer. The oral care layer is in contact with the anchor layer and forms an adhesive bond with the anchor layer; however, the oral care layer is minimally invested in the anchoring layer. When hydrated, the oral care layer has an adhesiveness relative to the surface of a user's teeth that is sufficient to retain the device on the user's teeth when placed thereon. The tooth whitening agent is delivered by wetting the teeth or the device, placing the device over the teeth, and conforming the device to the teeth by manual pressure so that the oral care layer is in contact with at least the front surface of the teeth. The device is then left on the teeth for a sufficient time to achieve the desired result whereupon it is removed from the teeth and discarded. The process of delivering the tooth whitening agent can be repeated as necessary.

The invention further provides a method of making a device for delivering an oral care agent, which device comprises permanently deformable backing layer, an anchor layer overtop the backing layer, and an oral care layer overtop the anchor layer. The device is sized to fit over a plurality of teeth in an upper or lower dental arch of a subject. The oral care layer comprises at least one oral care agent and at least one hydrophilic polymer. The oral care layer is in contact with the anchor layer and forms an adhesive bond with the anchor layer; however, the oral care layer is minimally invested in the anchoring layer. When hydrated, the oral care layer has an adhesiveness relative to the surface of a user's teeth that is sufficient to retain the device on the user's teeth when placed thereon. The method of making the device comprises the steps of providing the permanently deformable backing layer, attaching the anchor layer to the backing layer, and extruding the oral care layer onto the anchor layer.

DETAILED DESCRIPTION OF THE INVENTION

Figure 1:
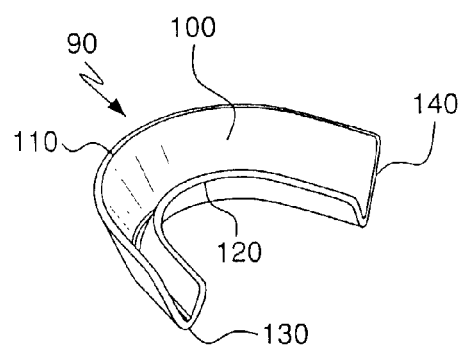
FIG. 1 is an isometric view of one embodiment of a device of the invention as seen from the back.

The invention concerns devices which deliver an oral care agent to the surface of the teeth. The present devices are particularly well-suited to delivering a tooth whitening agent to the surface of the teeth.

The construction of the device, and the characteristics of the various layers which comprise the device, serve to overcome the disadvantages of prior commercial or over-the-counter delivery systems discussed above. For example, the present device contains a pre-measured amount of oral care agent in an oral care layer, so there is no danger of over- or under-filling by the user. Because the oral care agent is not dispensed into the device by the user, the chance of contamination of the oral care layer by improper or careless filling of the device is eliminated. Moreover, the physical characteristics of the oral care layer are such that oral care agent does not spill or squeeze out into the oral cavity in appreciable quantities when the device is placed on the teeth.

The present device can be configured so that the user does not contact the oral care agent during routine manipulation of the device into place over the dental arch, but rather contacts only the backing layer. In any event, the oral care layer is sufficiently secured to the device by an anchor layer so that no residue is left on the user's fingers if the oral care layer is inadvertently touched. Moreover, no or minimal residue of the oral care layer is left on the teeth upon removal of the device. In some embodiments, as discussed in more detail below, the oral care agent is activated and/or released from the oral care layer over time, so that efficacy of the agent is maximized and the number and duration of each application is reduced.

All percentages given herein are by weight.

The device of the invention comprises three layers: a permanently deformable backing layer; an anchor layer attached to one side of the backing layer; and an oral care layer disposed on and attached to the anchor layer.

The backing layer comprises a thin, flexible layer of permanently deformable material. As used herein "permanently deformable" means that the backing layer retains any shape into which it is formed by application of slight pressure e.g., less than about 250,000 Pascals per square centimeter. Thus, the device readily conforms to the surface of the teeth and adjoining soft tissue across the dental arch in the user's mouth without tearing, cracking or breaking. The material which comprises the backing layer preferably has visco-elastic properties which allow the backing layer to creep as well as bend when pressure is applied to the device.

For example, a user can form the device around the teeth of the upper or lower dental arch by applying normal manual pressure to the backing layer with the tips of the fingers and thumbs. Assuming the surface area of the average adult finger or thumb tip is approximately one square centimeter, the normal pressure generated by the finger and thumb tips is about 100,000 to about 150,000 Pascals (i.e., about 3 lbs. or 1.36 kg) per square centimeter. The pressure is typically applied to the device by each finger and thumb tip for about one or two seconds. Once the pressure applied to the backing layer by the tips of the fingers and thumbs is removed, the device retains the shape of the dental arch and surface of the teeth and adjoining soft tissue onto which it was formed.

As used herein, "adjoining soft tissue" means the tissue surrounding the tooth structure, including the marginal gingiva, gingival sulcus, inter-dental gingiva, and the gingival gum structure on the lingual and buccal surfaces up to and including the muco-gingival junction and the pallet.

The backing layer can be any thickness which allows it to retain its permanently deformable characteristics; i.e., the layer cannot be so thin as to fail to retain its shape after application of pressure, and the layer cannot be so thick as to resist deformation. Preferably, the backing layer is from about 0.025 mm to about 2 mm thick, more preferably about 0.125 to about 0.8 thick, particularly preferably about 0.75 mm thick.

The backing layer preferably comprises a non-polymeric material such as a wax (e.g., microcrystalline or paraffin waxes), a tackifier (e.g., a natural or synthetic resin, such as a hydrocarbon resin), or mixtures thereof that have the properties discussed above.

Paraffin waxes are low-molecular weight waxes composed of straight-chain hydrocarbons, with melting points ranging from 48° C. to 75° C. These waxes are typically highly refined and have a low oil content. The paraffin waxes can be obtained by the distillation of crude oil, or can be produced synthetically, for example by Fischer-Tropsch synthesis. Paraffins produced by Fischer-Tropsch synthesis contain straight chain hydrocarbon molecules comprising methylene groups, which may have either even or odd numbers of carbons. The synthetic paraffins typically have a molecular weight range from about 300 g/mol to about 1400 g/mol, and melting points of about 48° C. to 75° C.

Microcrystalline waxes are flexible and amorphous-like in appearance, and have a higher tensile strength and smaller crystals than the paraffin waxes. The molecular weight of the commercially available microcrystalline waxes is generally from about 580-700 g/mol, with the average molecule containing 41-50 carbon atoms. Straight-chain molecules may be present in the microcrystalline waxes, but the largest proportion of molecules are branched-chain hydrocarbons and some ring-type compounds. The melting point of microcrystalline waxes is typically higher than the paraffin waxes; e.g., from about 60° C. to about 95° C.

Preferred microcrystalline and paraffin waxes for use in the present invention, and their physical characteristics, are given below in Table 1. A particularly preferred wax is Microcrystalline 180/185 (#146), available from Koster-Keunen, Inc., Watertown, Conn., 06795. Other suitable waxes include #165 sheet wax, available from Freeman Mfg. & Supply Co., Avon, Ohio, 44011-1011.

TABLE 1

| Wax | Congealing Point (ASTM D938) | Melting Point | Acid Value (USP 401) | Saponification Value (USP 401) | Penetration (ASTM D1321) | Viscosity (ASTM D2161) | Oil Content (wt %; ASTM D721) | Color (Visual) |
|---|---|---|---|---|---|---|---|---|
| Microcrystalline 180/185 (#146)[1] | 77-81° C. | 77-85° C. | <1 | <1 | 10-16, 100 g, 5s, @25° C. | 70-84@99° C. | 1.5% max | white to light yellow |
| Microcrystalline 193/198 (#118P)[1] | 80-92° C. | 89-92° C. | <1 | <1 | 5-9, 100 g, 5s, @25° C. | — | — | light yellow |
| Paraffin 140/145 (#126G)[1] | 82-92° C. | 60-63° C. | 0.1 max | 0.1 max | 11-18, 100 g, 5s, @25° C. | — | 1.5% max | — |
| Microcrystalline Wax S.P. 16[2] | — | 82-88° C. | nil | nil | 13-19, 100 g, 5s, @25° C. | 75-90@99° C. | — | yellow |
| synthetic paraffin[1] (CAS 8002-74-2) | 78-105° C. | — | — | — | — | — | not greater than 0.75% | white |

[1]Available from Koster-Keunen, Inc., Watertown, CT, 06795.
[2]Available from Strahl & Pitsch, Inc., West Babylon, NY, 11704.

The backing layer can also comprise hydrocarbon resins. Hydrocarbon resins are amorphous, glassy, typically low molecular weight hydrocarbons with defined molecular weight ranges. Hydrocarbon resins suitable for producing the backing layer include the "Escorez" 5300 series of water-white, clear cycloaliphatic hydrocarbon resins (CAS #68132-00-3) available from ExxonMobil Chemical, Houston, Tex. 77079-1398. A preferred hydrocarbon resin is Escorez 5380. The typical physical characteristics of the Escorez 5300 series hydrocarbon resins are given in Table 2 below.

TABLE 2

| Resin | 5380 | 5300 | 5320 | 5340 | ExxonMobil Test Method[2] |
|---|---|---|---|---|---|
| Softening Point, R&B, ° C. | 85 | 105 | 122 | 140 | ETM 22-24 |
| Color | | | | | |
| Ylt, initial[1] | 1 | 1 | 1 | 1 | ETM 22-13 |
| Yl, Aged 5 hours at 175° C.[1] | 3 | 3 | 3 | 3 | ETM 22-14 |
| Molten Gardner Color | 1 | 1 | 1 | 1 | ETM 22-12 |
| Melt Viscosity (Brookfield) | | | | | ETM 22-31 |
| Test Temperature, ° C. | 140 | 140 | 160 | 180 | |
| Cps | 700 | 4,500 | 5,000 | 4,500 | |
| Molecular Weight | | | | | ETM 300-83 |

TABLE 2-continued

| Resin | 5380 | 5300 | 5320 | 5340 | ExxonMobil Test Method[2] |
|---|---|---|---|---|---|
| $\overline{M}w$ | 370 | 420 | 430 | 460 | |
| $\overline{M}n$ | 160 | 210 | 190 | 230 | |
| $\overline{M}z$ | 900 | 900 | 950 | 1000 | |
| Tg, ° C. | 35 | 55 | 65 | 85 | ETM 300-90 |
| Specific Gravity, 20/20° C. (IPOH) | 1.1 | 1.1 | 1.1 | 1.1 | ETM 22-28 |
| Ash Content, wt. % | <0.1 | <0.1 | <0.1 | <0.1 | ETM 22-05 |
| Acid Number, mg KOH/g | <1 | <1 | <1 | <1 | ETM 22-49 |
| Volatility, wt % | 10.0 | 4.0 | 1.5 | 0.5 | ETM 22-32 |

[1]Solution color as determined by measurement of a 50% (by weight) product in toluene mixture.
[2]The entire disclosures of the ExxonMobil Test Methods are herein incorporated by reference.

The backing layer can optionally be colored, so that the device is obtrusive when worn. For example, the backing layer (and thus the device itself) can be colored with bright or vibrant colors which a consumer may find pleasing. The backing layer can therefore comprise a colorizing compound, such as, for example, a dye, pigment or substance that can impart color when added to the material forming the backing layer.

For example, colorizing compounds of the type commonly used with a food, drugs, or cosmetics in connection with the human body, especially color additives permitted for use in foods which are classified as "certifiable" or "exempt from certification," can be used to color the backing layer. The colorizing compounds used to color the backing layer can be derived from natural sources such as vegetables, minerals or animals, or can be man-made counterparts of natural derivatives.

Colorizing compounds presently certified under the Food Drug & Cosmetic Act for use in food and ingested drugs include dyes such as FD&C Red No. 3 (sodium salt of tetraiodofluorescein); Food Red 17 (disodium salt of 6-hydroxy-5-{(2-methoxy-5-methyl-4-sulphophenyl)azo}-2-naphthalenesulfonic acid); Food Yellow 13 (sodium salt of a mixture of the mono and disulfonic acids of quinophthalone or 2-(2-quinolyl)indanedione); FD&C Yellow No. 5 (sodium salt of 4-p-sulfophenylazo-1-p-sulfophenyl-5-hydroxypyrazole-3 carboxylic acid); FD&C Yellow No. 6 (sodium salt of p-sulfophenylazo-B-napthol-6-monosulfonate); FD&C Green No. 3 (disodium salt of 4-{[4-(N-ethyl-p-sulfobenzylamino)-phenyl]-(4-hydroxy-2-sulfonium-phenyl)-methylene}-[1-(N-ethyl-N-p-sulfobenzyl)-3,5-cyclohexadien-imine]); FD&C Blue No. 1 (disodium salt of dibenzyldiethyldiaminotriphenylcarbinol trisulfonic acid anhydrite); FD&C Blue No. 2 (sodium salt of disulfonic acid of indigotin); FD&C Red No. 40; Orange B; and Citrus Red No. 2; and combinations thereof in various proportions.

Colorizing compounds exempt from FDA certification include annatto extract; beta-apo-8'-carotenal; beta-carotene; beet powder; canthaxanthin; caramel color; carrot oil; cochineal extract (carmine); toasted, partially defatted, cooked cottonseed flour; ferrous gluconate; fruit juice; grape color extract; grape skin extract (enocianina); paprika; paprika oleoresin; riboflavin; saffron; turmeric; turmeric oleoresin; vegetable juice; and combinations thereof in various proportions.

The form of the colorizing compound for use in the present invention preferably includes dye form additives, but may also include lake forms which are compatible with the material comprising the backing layer. Water soluble dyes, provided in the form of powders, granules, liquids or other special-purpose forms, can be used in accordance with the present method. Preferably, the "lake", or water insoluble form of the dye, is used for coloring the backing layer. For example, if a suspension of a colorizing compound is to be used, a lake form additive can be employed. Suitable water insoluble dye lakes prepared by extending calcium or aluminum salts of FD&C dyes on alumina include FD&C Green #1 lake, FD&C Blue #2 lake, FD&C R&D #30 lake and FD&C # Yellow 15 lake.

Other suitable colorizing compounds include non-toxic, water insoluble inorganic pigments such as titanium dioxide; chromium oxide greens; ultramarine blues and pinks; and ferric oxides. Such pigments preferably have a particle size in the range of about 5 to about 1000 microns, more preferably about 250 to about 500 microns.

The concentration of the colorizing compound in the backing layer is preferably from about 0.05% to about 10%, and is more preferably from about 0.1% to about 5%.

More than one colorizing compound can be present in the backing layer, so that multiple colors are imparted to the backing layer. The multiple colors in the backing layer can be patterned into stripes, dots, swirls or any other design which a consumer may find pleasing. The colorizing compound can also be used with other appearance-enhancing substances such as glitter particles.

The backing layer can also be embedded or decorated with decorative items such as beads, rhinestones, or the like, as long as these items do not interfere with the properties of the backing layer required for proper deformation of the device onto the teeth, as described above. The backing layer can also display letters, words, or images designed to be pleasing or attractive to a consumer.

The anchor layer preferably comprises a thin, flexible layer of open-cell foam which is located immediately adjacent to the backing layer. The opposing faces of the backing and anchor layer material are in contact with one another essentially along their entire surfaces, and the material comprising the backing layer penetrates slightly into spaces between the cells of the opposing side of the foam forming the anchor layer. Preferably, the face of the backing layer contacting the anchor layer is softened by heating prior to laminating the backing layer to the anchor layer.

In one embodiment, the anchor layer is co-extensive with the backing layer. As used herein, "coextensive" means having substantially the same length and width as the backing layer. In other embodiments, the anchor layer is of smaller dimensions (i.e., in length and/or width) than the backing layer, so that the material comprising the backing layer extends beyond one or more edges of the anchor layer when the two layers are in contact.

The anchor layer preferably has minimal flexural stiffness; that is, the anchor layer does not resist deformation when the device is pressed into place on the teeth of the user. Thus, the anchor layer can be any thickness which does not interfere with the permanent deformation of the device when pressure is applied by the user. Preferably, the anchor layer is from about 0.025 mm to about 1 mm thick, more preferably about 0.6 mm to about 0.8 mm thick.

The anchor layer preferably comprises an open-cell foam such as a polyurethane, polystyrene or polyethylene foam. A preferred open-cell foam is a polyether-based reticulated open-cell polyurethane foam. The anchor layer may also comprise a color or pigment, which imparts a color or hue to the anchor layer. In embodiments where the backing layer is uncolored but the anchor layer is colored, the color of the anchor layer is preferably visible, thus making the device obtrusive when worn. The anchor layer can comprise the same colorizing compounds in the same preferred concentrations listed above for coloring the backing layer.

The oral care layer comprises at least one oral care agent and at least one hydrophilic polymer, and is located immediately adjacent to the side of the anchor layer which is not attached to the backing layer. The opposing faces of the oral care and anchor layers are in contact with one another and form an adhesive bond between those layers. The oral care layer is disposed on the anchor layer and is minimally invested in the foam. As used herein, "minimally invested" means that the oral care layer fills only the surface depressions in the anchor layer foam, but does not appreciably penetrate below the surface of the anchor layer. The oral care layer is generally co-extensive with the anchor layer.

The oral care layer has minimal flexural stiffness; that is, the oral care layer does not resist deformation when the device is pressed into place on the teeth of the user. Thus, the oral care layer can be any thickness which does not interfere with the permanent deformation of the device when pressure is applied by the user, and which allows a suitable amount of oral care agent to be contained within the layer for delivery to the teeth. Preferably, the oral care layer is from about 0.025 mm to about 4 mm thick, more preferably about from about 0.125 mm to about 1.5 mm thick, particularly preferably from about 0.25 mm to 1.0 mm, for example about 0.3 mm, thick.

The oral care layer has an adhesiveness when hydrated which is sufficient to adhere the surface of the teeth and surrounding soft tissue when the device is conformed to the teeth and dental arch. The oral care layer should adhere to the teeth and surrounding soft tissue for as long a period of time as necessary for the oral care agent to be delivered and effect the desired result. Typically, the device is left on the teeth for approximately 15 minutes to one hour, although shorter or longer times are contemplated. Methods for delivering an oral care agent to the teeth with the present device are described in more detail below.

The oral care layer also has sufficient adhesiveness to the teeth and cohesiveness so that the device is resistant to inadvertent removal and yet is easily removed from the teeth. The strength of the adhesive bond between the oral care layer and the teeth is preferably less than the strength of the adhesive bond between the oral care and anchor layers. Furthermore, the adhesive properties of the oral care layer should not be weakened or destroyed by exposure to moisture or high humidity. In one embodiment, the adhesive properties of the oral care layer with respect to bonding to the teeth are enhanced by hydration, for example with water or saliva.

As used herein, "adhesion" or "adhesiveness" refers to the molecular attraction exerted between surfaces of bodies in contact. As used herein, "cohesion" or "cohesiveness" refers to the molecular attraction by which the particles of a body are united throughout the mass.

Adhesiveness can be expressed in units of force per distance (e.g., "Newtons/meter" or "N/m"), and cohesiveness can be expressed in terms of tack. A suitable strength for an adhesive bond between the oral care layer and the surface of the teeth ranges from about 200 to about 400 N/m. A suitable tack for the oral care layer is greater than about 50 g/cm$^2$.

Adhesiveness and tack can be measured by standard tests such as 90 or 180 degree peel force tests, rolling ball-style tests, tack tests (e.g., the PKI or TRBT tack determination methods), and static shear tests, and other tests such as are known in the art.

For example, a modified commercially available surface tensiometer suitable for measuring the adhesive strength of bioadhesives is described in U.S. Pat. No. 4,615,697 of Robinson, the entire disclosure of which is herein incorporated by reference. The adhesiveness and tack of the present oral care layer can also be determined using a TA.XT2 Texture Analyzer (Texture Technologies Corp.) together with an XT.RA Dimension software package (Stable Micro Systems, Ltd.), according to the manufacturer's instructions.

According to the operation of a TA.XT2 texture analyzer, the device for testing is mounted on a block with the oral care layer exposed, and a probe attached to the TA.XT2 texture analyzer is moved at a fixed speed against the adhesive surface of the oral care layer, distorting the oral care layer to a fixed penetration depth. The probe is permitted to dwell at the penetration depth for a fixed time. The probe is then withdrawn from the oral care layer at a fixed speed, and the peak force required to detach the probe from the oral care layer surface is measured. Suitable conditions for measuring the adhesiveness and tack of the present oral care layer with the TA.XT2 Texture Analyzer are a probe diameter of 0.80 cm, a penetration depth of 0.1 mm, a penetration rate of 1.0 mm/sec, a dwell time of 10 sec, and a withdrawal rate of 5.0 mm/sec.

In some embodiments, the oral care agent is entrapped within the oral care layer by a matrix formed by the hydrophilic polymer. The oral care agent is released from the hydrophilic polymer matrix upon hydration and swelling of the hydrophilic polymer, whereupon the agent is delivered to the teeth to produce the desired effect.

Preferably, prior to release and/or activation with water or saliva, the oral care agent within the oral care layer is stable such that essentially no potency is lost during normal storage conditions for greater than one year prior to use.

Preferably, the oral care layer comprises a pressure-sensitive adhesive comprising an oral care agent and a hydrophilic polymer that is made tacky (that is, it is rendered pressure-sensitive) at room temperature by addition of a water-soluble plasticizer that is miscible with the polymer.

Hydrophilic polymers useful in the oral care layer are characterized as being solid at room temperature; that is, as having a glass transition temperature T(g), or melting point T(m), higher than about 25° C. and lower than about 120° C., and more preferably higher than about 30° C., and lower than about 100° C. The hydrophilic polymers also preferably have a hydrophilicity as measured by water uptake greater than about 25%. Suitable polymers include polysaccharides (e.g., starches and starch derivatives, cellulose-derivatives such as sodium carboxymethyl cellulose or "Na—CMC"), and water-soluble synthetic polymers (e.g., 2-acrylamido-2-methyl-propanesulfonic acid or "poly AMPS", polyvinyl pyrrolidone or "PVP," polyvinyl alcohol or "PVA," hydroxypropyl cellulose or "HPC", polyethylene oxide or "PEO", polyacrylic acid or "P," and carboxylic acid polymers such as the Carbopols and Carbomers available from B. F. Goodrich); polypeptides; and natural gums such as xanthan gum, karaya gum, and gelatin.

Plasticizers useful in the oral care layer are characterized as being liquid at room temperature and having a boiling point higher than about 80° C. Suitable plasticizers include glycerin, sorbitol, any of the glycols, polysorbate 80, triethyl titrate, acetyl triethyl titrate, and tributyl titrate.

Preferably, the hydrophilic polymer comprising the oral care layer comprises crosslinked or non-crosslinked polymers such as 2-acrylamido-2-methyl-propanesulfonic acid (poly AMPS); polyvinyl pyrrolidone (PVP); polyethylene oxide (PEO); polyacrylates (e.g., the Eudragits™, available from Rohm America, Inc., Piscataway, N.J.); polyvinyl alcohol (PVA); carboxylic acid polymers (e.g., Carbopols™ and Carbomers™ available from B. F. Goodrich). The Eudragits are characterized as (1) an anionic copolymer based on methacrylic acid and methylmethacrylate wherein the ratio of free carboxyl groups to the ester groups is approximately 1:1, (2) an anionic copolymer based on methacrylic acid and methylmethacrylate wherein the ratio of free carboxyl groups to the ester groups is approximately 1:2, (3) a copolymer based on acrylic and methacrylic acid esters with a low content of quaternary ammonium groups wherein the molar ratio of the ammonium groups to the remaining neutral methacrylic acid esters is 1:20, and (4) a copolymer based on acrylic and methacrylic acid esters with a low content of quaternary ammonium groups wherein the molar ratio of the ammonium groups to the remaining neutral methacrylic acid esters is 1:40.

Particularly preferred are oral care layers comprising the poly(AMPS)-based pressure sensitive adhesives described in U.S. Pat. No. 4,581,821 of Cahalan et al., or comprising the PEG-PVP-based pressure sensitive adhesives described in U.S. Published Application No. 2002/0037977 of Feldstein et al, the entire disclosures of which are herein incorporated by reference.

The oral care layer can also comprise a scrim, which serves to reinforce the oral care layer against fragmentation and delamination from the anchor layer. The scrim is preferably imbedded in the oral care layer, and can comprise a variety of woven or non-woven materials or perforated sheetlike materials which are known in the art. Suitable woven materials for forming the scrim include cloth or gauze formed of natural or synthetic fibers such as cotton; polyester (e.g., DACRON® fibers, and SONTARA® fabrics such as polyester grades 8000, 8027 and 8100, E. I. dupont de Nemours & Co.); polyolefins (e.g., polyethylene, polypropylene and the like); polyurethane; polyamide (e.g., NYLON® fiber); polyaramide (e.g., KEVLAR® fiber); and glass (e.g., FIBERGLAS™ fiber). The woven materials for forming the scrim can be a conventional weave or a nonconventional weave, such as either of the "hook" or "loop" fabrics used in hook and loop fasteners.

Suitable nonwoven materials for forming the scrim include felt and synthetic fibers such as polyester; polyolefins (e.g., polyethylene, polypropylene and the like); polyurethane; polyamide (e.g., NYLON® fiber); polyaramide (e.g., KEVLAR® fiber); and glass (e.g., FIBERGLAS™ fiber). Particularly preferred is a non-woven polyolefin fabric, such as DELNET® fabric from DelStar Technologies, Inc. (Middletown, Del.).

Suitable perforated sheetlike materials for forming the scrim include fine pitch polypropylene net.

Preferably, the scrim should be free of objectionable taste or odor, and be safe for use in the mouth. The material forming the scrim also preferably has a melting temperature above the melting or softening temperature of the material forming the oral care layer.

In a preferred embodiment, the scrim is embedded in the oral care layer. The scrim can be embedded in the oral care layer by techniques well-known in the art. For example, the scrim can be sandwiched between two layers of material that make up the oral care layer. The oral care layer can also be extruded directly onto the scrim, whereupon the melted material comprising the oral care layer flows through and around the openings in the scrim material. Upon cooling of the melted oral care layer material, the scrim is entirely surrounded by the oral care layer. Other methods for embedding non-woven, woven or perforated sheet scrims in the oral care layer will be apparent to those of ordinary skill in the art.

In one embodiment, the material comprising the oral care layer releases the oral care agent over time, so that activated oral care agent is delivered to the teeth throughout the entire period during which the device is used. Such oral care layers are called "sustained-release" oral care layers. In one embodiment, oral care agent is delivered to the teeth in a substantially uniform quantity per unit time by the sustained-release oral care layer. In another embodiment, oral care agent is delivered in non-uniform quantities per unit time. For example, larger quantities of activated oral care agent can be delivered in a given portion of the treatment period as compared to the other portions; e.g., more oral care agent can be delivered during the first quarter, third or half of the treatment period than in the remaining portions of the treatment period.

The sustained-release oral care layer delivers the oral care agent by diffusion of the oral care agent through the oral care layer toward the surface of the teeth and surrounding tissue. Diffusion outward into the oral cavity is blocked by the backing layer, which is substantially impermeable to the oral care agent and to saliva under the conditions in which the device is used. A limited amount of oral care agent may escape into the oral cavity by diffusion outward from the edges of the device during use; however, this should have a negligible impact on the safety and efficacy of the device. It is preferred that the oral care layer is not substantially degradable or erodable, so that little to no degradation by-products are produced and released into the oral cavity during use of the device.

The rate of delivery of the oral care agent from the oral care layer to the teeth can be controlled by adjusting the concentration of hydrophilic polymer and plasticizer in the oral care layer. Generally, a higher concentration of hydrophilic polymer in the oral care layer results in a higher cohesive strength of the layer, which in turn lowers the rate of release of the oral care agent. The cohesiveness of hydrophilic polymer-based materials suitable for use in the oral care layer can be adjusted to a desired value according to principles well-known in the art; see, for example, U.S. Pat. No. 4,581,821 of Cahalan et al., supra, and U.S. Published Application No. 2002/0037977 of Feldstein et al., supra.

The concentration of oral care agent in the oral care layer required to deliver the desired amount of oral care agent to the teeth and surrounding tissue can vary depending on factors such as the type, length and frequency of treatment to be performed, the severity of the condition, the age and health of the user, and the like. One of ordinary skill in the art can readily vary the concentration of the oral care agent in the oral care layer in order to achieve a desired result. Generally, the amount of oral care agent in the oral care layer is from preferably about 0.01% to about 40%, preferably from about 0.1% to about 20%, more preferably from about 0.5% to about 10%, and most preferably from about 1% to about 7%. Preferred amounts of a given oral care agent to be included in the oral care layer are provided below.

The oral care agent can be any pharmaceutically active agent useful in treating physiological conditions involving the teeth and surrounding tissue. As used herein, a "pharmaceutically active agent" is any substance that can be released from the oral care layer to treat an undesirable physiological condition. Undesirable, physiological conditions involving the teeth or surrounding tissue which are amenable to treatment with the present device include: halitosis; periodontal and oral infections; periodontal lesions; dental caries or decay; gingivitis; and other periodontal diseases.

The pharmaceutically active oral care agent can be, for example, an non-steroidal anti-inflammatory/analgesic (preferably 0.1-5% in the oral care layer); steroidal anti-inflammatory agents (preferably 0.002-0.5% in the oral care layer); local anesthetics (preferably 0.05-2% in the oral care layer); bactericides/disinfectants (preferably 0.01-10% in the oral care layer); antibiotics (preferably 0.001-10% in the oral care layer); antifungals (preferably 0.1-10% in the oral care layer); tooth desensitizing agents (preferably 0.1-10% in the oral care layer); fluoride anticavity/antidecay agents (preferably 50 ppm to 10,000 ppm in the oral care layer); anti-tartar/anti-calculus agents; enzymes which inhibit the formation of plaque, calculus or dental caries; and nutritional supplements for local delivery to the teeth and surrounding tissue.

Suitable non-steroidal anti-inflammatory/analgesic agents include acetaminophen; methyl salicylate; monoglycol salicylate; aspirin; mefenamic acid; flufenamic acid; indomethacin; diclofenac; alclofenac; diclofenac sodium; ibuprofen; flurbiprofen; fentizac; bufexamac; piroxicam; phenylbutazone; oxyphenbutazone; clofezone; pentazocine; mepirizole; and tiaramide hydrochloride.

Suitable steroidal anti-inflammatory agents include hydrocortisone; prednisolone; dexamethasone; triamcinolone acetonide; fluocinolone acetonide; hydrocortisone acetate; prednisolone acetate; methylprednisolone; dexamethasone acetate; betamethasone; betamethasone valerate; flumetasone; flouromethholone; budesonide; and beclomethasone dipropionate.

Suitable local anesthetics include dibucaine hydrochloride; dibucaine; lidocaine hydrochloride; lidocaine; benzocaine; p-buthylaminobenzoic acid 2-(diethylamino)ethyl ester hydrochloride; procaine hydrochloride; tetracaine hydrochloride; chloroprocaine hydrochloride; oxyprocaine hydrochloride; mepivacaine; cocaine hydrochloride; and piperocaine hydrochloride.

Suitable bactericides/disinfectants include thimerosol; phenol; thymol; benzalkonium chloride; benzethonium chloride; chlorhexidine; providone iodide; cetylpyridinium chloride; eugenol, and trimethylammonium bromide.

Suitable antibiotics include penicillin; meticillin; oxacillin; cefalotin; cefaloridin; erythromycin; lincomycin; tetracycline; chlortetracycline; oxytetracycline; metacycline; chloramphenicol; kanamycin; streptomycin; gentamicin; bacitracin; and cycloserine.

Suitable antifungal drugs include amphotericin; clotrimazole; econazole nitrate; fluconazole; griseofulvin; itraconazole; ketoconazole; miconazole; nystatin; terbinafine hydrochloride; undecenoic acid; and zinc undecenoate.

Suitable tooth-desensitizing agents include potassium nitrate and strontium chloride.

Suitable fluoride anticavity/antidecay agents include sodium fluoride, potassium fluoride and ammonium fluoride.

Suitable anti-tartar/anti-calculus agents include phosphates such as pyrophosphates, polyphosphates, polyphosphonates (e.g., ethane-1-hydroxy-1,1-diphosphonate, 1-aza-cycloheptane-1,1-diphosphonate, and linear alkyl diphosphonates), and salts thereof; linear carboxylic acids; and sodium zinc citrate; and mixtures thereof. Preferred pyrophosphate salts are the dialkali metal pyrophosphate salts, tetra-alkali metal pyrophosphate salts; and the hydrated or unhydrated forms of disodium dihydrogen pyrophosphate ($Na_2H_2P_2O_7$—), tetrasodium pyrophosphate ($Na_4P_2O_7$), and tetrapotassium pyrophosphate ($K_4P_2O_7$). The pyrophosphate salts are described in more detail in Kirk & Othmer, Encyclopedia of Clinical Technology Third Edition, Volume 17, Wiley-Interscience Publishers (1982), the entire disclosure of which is herein incorporated by reference in its entirety.

Suitable enzymes which inhibit the formation of plaque, calculus or dental caries include: proteases that break down salivary proteins which are absorbed onto the tooth surface and form the pellicle, or first layer of plaque; lipases which destroy bacteria by lysing proteins and lipids which form the structural component of bacterial cell walls and membranes; dextranases, glucanohydrolases, endoglycosidases, and mucinases which break down the bacterial skeletal structure which forms a matrix for bacterial adhesion to the tooth; and amylases which prevent the development of calculus by breaking-up the carbohydrate-protein complex that binds calcium. Preferred enzymes include any of the commercially available proteases; dextranases; glucanohydrolases; endoglycosidases; amylases; mutanases; lipases; mucinases; and compatible mixtures thereof.

Suitable nutritional supplements for local delivery to the teeth and surrounding tissue include vitamins (e.g., vitamins C and D, thiamine, riboflavin, calcium pantothenate, niacin, folic acid, nicotinamide, pyridoxine, cyanocobalamin, para-aminobenzoic acid, and bioflavonoids); and minerals (e.g., calcium, phosphorus, fluoride, zinc, manganese, and potassium); and mixtures thereof. Vitamins and minerals useful in the present invention are disclosed in *Drug Facts and Comparisons* (loose leaf drug information service), Wolters Kluer Company, St. Louis, Mo., 1997, pp 3-17; the entire disclosure of which is herein incorporated by reference.

The oral care agent can also be any cosmetically active agent. As used herein, a "cosmetically active agent" includes any substance that can be released from the oral care layer to effect a desired change in the appearance of the teeth or surrounding tissue, or which imparts a socially desirable characteristic to the user, such as fresh breath. For example, a cosmetically active agent can be a breath freshener or an agent which effects whitening or bleaching of the teeth. Recognizing that in some cultures or in certain segments of Western society coloration of the teeth may be significant or desirable, the cosmetically active agent can also be any agent which imparts a color or tint to the teeth.

Suitable tooth whitening agents include peroxides, metal chlorites, perborates, percarbonates, peroxyacids, and combinations thereof. Suitable peroxide compounds include hydrogen peroxide, calcium peroxide, carbamide peroxide, and mixtures thereof. The preferred peroxides are hydrogen and carbamide peroxide. Suitable metal chlorites include calcium chlorite, barium chlorite, magnesium chlorite, lithium chlorite, sodium chlorite, and potassium chlorite; hypochlorite and chlorine dioxide. The preferred chlorite is sodium chlorite.

The preferred concentration of tooth whitening agent in the oral care layer of from about 0.01% to about 40%. If a peroxide compound is chosen as the tooth whitening agent, the peroxide compound should be equivalent to about 0.1% to about 20% of hydrogen peroxide, preferably from about 0.5% to about 10% of hydrogen peroxide, and most preferably from about 1% to about 7% of hydrogen peroxide, for example 6% of hydrogen peroxide.

As used herein, a "hydrogen peroxide equivalent" is the amount of peroxide compound necessary to deliver the same amount of hydroxyl radicals as a given amount of hydrogen peroxide. For example, it takes 3 moles of carbamide peroxide to deliver the same number of hydroxyl radicals as 1 mole of hydrogen peroxide. Therefore, to deliver the hydrogen peroxide equivalents disclosed in the preceding paragraph, carbamide peroxide should generally present in an amount of from about 0.3% to about 60% and preferably from about 1.5% to about 30%, particularly preferably from about 3% to about 21%, for example 18%, in the oral care layer.

The oral care layer can also comprise additional ingredients which do not alter the adhesive, cohesive or structural properties of the layer, or interfere with the delivery of the oral care agent. Such additional ingredients include coloring compounds as described above; food additives; flavorants; sweeteners; and preservatives.

Any natural or synthetic flavorant or food additive, such as those described in Chemicals Used in Food Processing, Pub. No. 1274, National Academy of Sciences, pages 63-258 (the entire disclosure of which is herein incorporated by reference) can be used. Suitable flavorants include wintergreen, peppermint, spearmint, menthol, fruit flavors, vanilla, cinnamon, spices, flavor oils and oleoresins, as known in the art. The amount of flavorant employed is normally a matter of preference, subject to such factors as flavor type, individual flavor, and strength desired. Preferably, the oral care layer comprises from about 0.1% to about 5% flavorant.

Sweeteners useful in the present invention include sucrose, fructose, aspartame, xylitol and saccharine. Preferably, the oral care layer comprises sweeteners in an amount from about 0.001% to about 5.0%.

The device of the invention is preferably substantially non-flat as provided to the user. As used herein, "substantially non-flat" means that the device is bent, creased or curved along its long axis. For example, the device may have a "J", "reversed J", "V", "U", or "C" shape or the like when viewed in cross-section. The oral care layer is located to the inside of the bend or curve (e.g., the concave side), so that the oral care layer is protected from inadvertent contact by the user. In normal use and handling, the user should only touch the backing layer, which forms the outside of the device. In addition, the oral care layer can be protected with an optional release liner, or a covering enclosing the inside (e.g., the concave side) of device.

The release liner may be formed from any material which exhibits less affinity for the oral care substance than the oral care substance exhibits for itself and for the release liner material. The release liner preferably comprises a rigid sheet of material such as polyethylene, paper, polyester, or other material which is then coated with a non-stick type material. The release liner material can be coated with wax, silicone, teflon, fluoropolymers, or other non-stick type materials. A preferred release liner is Scotchpak(produced by 3M. The release liner may be cut to substantially the same size and shape as the oral care layer surface of the device, or the release liner may be cut larger than the oral care layer surface of the device to provide a readily accessible means for separating the material from the strip. The release liner may be formed from a brittle material which cracks when the device is flexed, or from multiple pieces of material or a scored piece of material. Alternatively, the release liner can comprise two overlapping pieces, such as a typical adhesive strip bandage design. In one embodiment, the optional release liner can be integral with a package enclosing the device. A further description of materials suitable for use as a release liner is found in *Kirk-Othmer Encyclopedia of Chemical Technology*, Fourth Edition, Volume 21, pp. 207-218, the entire disclosure of which is incorporated herein by reference. The covering enclosing the inside (e.g., the concave side) of the present device can be made of similar materials.

In addition to the curve, crease or bend which may be possessed by the device of the invention when viewed in cross section, the device is of an overall size and shape to fit over some or all of the teeth in either the upper or lower dental arch of the user's mouth. Although the present device can be used on primary, mixed or permanent dentition, for ease of reference the invention will be discussed in terms of the permanent dentition of an average adult human being.

An adult human user will typically have a permanent dentition composed of sixteen teeth in the upper dental arch, and sixteen teeth in the lower dental arch. As used herein, "dental arch" means an individual row of teeth forming a tooth row attached to either the upper or lower jaw bone. The curve of the dental arch is known as the catenary arch. Each dental arch has the following tooth types arranged symmetrically in the arch: four incisors or front teeth, two canines, four bicuspids and six molars. The incisors and canines are called the anterior teeth, and the bicuspids and molars are called the posterior teeth. The shape of the anterior teeth is generally the same for the upper and lower dental arch, with the top set generally being larger. The posterior teeth are of generally the same size and shape in both the upper and lower dental arches.

Preferably, the device is of sufficient length to cover at least the facial surface of the incisors in a dental arch, and is of sufficient width to extend from the incisor facial surface, over the crowns, and at least partially cover the lingual surface of the incisors. Generally, the device will begin coverage of the facial surface of the teeth at the point where the facial surface contacts the gums. It is understood that the device may partially cover the gums or other surrounding tissue. As used herein, the "facial" surface of a tooth is the surface toward the cheeks or lips, and the "lingual" surface of a tooth is the surface toward the tongue.

In a more preferred embodiment, the device is of sufficient length and width to cover the facial surface, crowns and at least partially cover the lingual surface of the anterior teeth in a dental arch. Particularly preferred is a device having sufficient length and width to cover the facial surface, crowns and at least partially cover the lingual surface of the anterior and posterior teeth in a dental arch.

For a device designed to fit the upper dental arch, a suitable length is from about 7 cm to about 9 cm, and a suitable average width is from about 0.8 cm to about 2.5 cm. For a device designed to fit the lower dental arch, a suitable length is from about 4 cm to about 6 cm, and a suitable average width is from about 1 cm to about 2 cm. It is understood that the device is intended to fit a range of similarly-sized dental arches, and that the device, as used, is conformed to fit the dental arch of a particular user. Therefore, the dimensions presented herein are not intended to be limiting, but are rather presented as a guide for constructing the device. For example, devices designed for use in children or smaller adults are proportionally smaller than those described above for the normal-sized adult.

The device can be essentially any shape which allows sufficient coverage of the teeth, as discussed above. For example, when viewed in plan view, the device can be straight, or can be slightly bent; e.g., in conformity with the catenary arch of the upper or lower human dental arch. Where the device is designed to fit over all the teeth in a dental arch, the device is preferably bent into a horseshoe-shape that generally matches the catenary arch.

In flattened form and viewed in plan view, the device can be substantially rectangular in shape; e.g., having four edges which each pair of non-intersecting edges are close to parallel or are arched in the same way. For example, a device in which the "front" edge of the device and the "back" edge of the device are curved in the same way, and the side edges are essentially parallel or slightly off-parallel, is considered to be rectangular in shape; see, e.g., FIG. 12. As used herein, the "front" edge of the device is the long edge of that portion of the device placed against the facial surface of the teeth. As used herein, the "back" edge of the device is the long edge of that portion of the device placed against the lingual surface of the teeth. The "side" edges are the remaining edges of the device. The front and back edges are non-intersecting, and the "side" edges of the device are non-intersecting.

The device can also be substantially trapezoidal in shape when in flattened form and viewed in plan view. As used herein, "trapezoidal in shape" means any shape having four edges where the front and back edges are generally parallel or arched the same way, and the back edge is shorter than the front edge. The side edges are generally not parallel. For example, the device may be trapezoidal in shape when the front edge is convex and the back edge is concave and is also shorter than the front edge, and the side edges are not parallel; see, e.g., FIG. 13. The trapezoidal shape may help to reduce bunching or buckling of the device when placed on the dental arch, and allow the oral care layer more efficiently contact the surfaces of the teeth.

Alternatively, the shape of the device when in flattened form and viewed in plan view can be generally round, oval, or polygonal. It is understood that the shape of the device when in flattened form and viewed in plan view out does not have to be symmetrical. Moreover, the edges of the device need not be straight, but can be irregular.

Any or all of the edges of the device may be notched. By notched it is meant that there are one or more recesses, indentations, or curves of some type cut out of the device edge. The notches help prevent buckling of the device when the device is formed over the curve of the dental arch, and may be advantageously be placed in the back edge of the device. In a preferred embodiment, the back edge of the device contains a plurality of notches substantially evenly spaced along the back edge.

Certain embodiments of the device will now be illustrated with reference to the figures, where like reference numbers indicated like structures.

Figure 2:
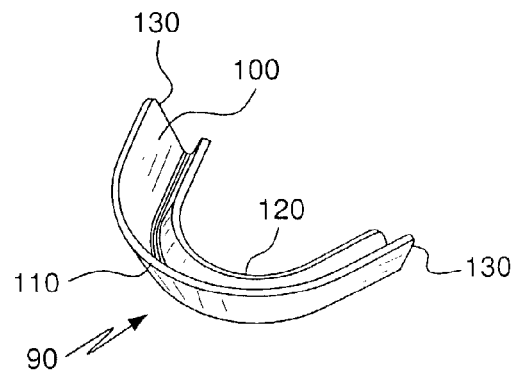
FIG. 2 is an isometric view of the device of FIG. 1 as seen from the front.

FIGS. 1 and 2 show back isometric and front isometric views, respectively, of an oral care delivery device of the invention generally designated as 90, which is designed to fit the upper dental arch. The device is bent into a horseshoe-shape that generally conforms to the catenary arch of a user. The inside 100 of the device, which is bounded by front edge 110, back edge 120, left side edge 130 and right side edge 140, contains the oral care layer.

Figure 3:
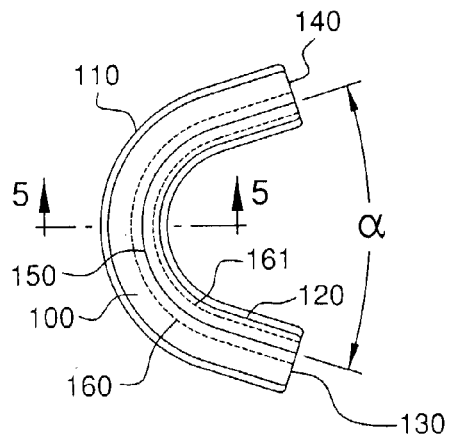
FIG. 3 is a top plan view of the of the device of FIG. 1.

FIG. 3 shows a top plan view of the device of FIGS. 1 and 2. Line 5-5 in FIG. 3 bisects the device along a line corresponding to the medial line of a dental arch, and defines the two arms of the horseshoe. The horseshoe arms are set at angle α of approximately 36°, generally corresponding to the angle of a user's teeth in the catenary arch. Main fold line 150 and secondary fold lines 160 and 161 extend from left side edge 130 to right side edge 140 along the long axis of the device. Generally, the fold lines are formed when the device is pressed or vacuum formed into a forming die during the folding process; however, other methods of producing the fold lines (e.g., etching or gouging) such as are known in the art can also be used.

Figure 4:
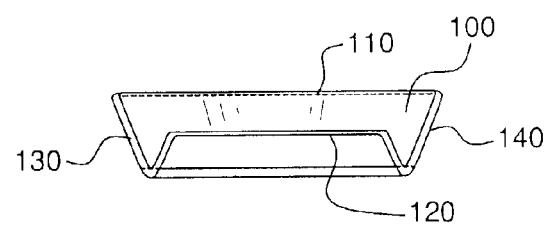
FIG. 4 is a back view of the device of FIG. 1.

The device is folded along the main and secondary fold lines, with the oral care layer to the inside 100 of the device, and the backing layer to the outside. The main fold line 150 and secondary fold lines 160 and 161 are offset towards back edge 120 of the device. Folding of the device along the offset fold lines provides a portion of the inside of the device from the front edge to the fold lines which is larger than the portion of the device from the back edge to the fold lines. This larger portion is intended to contact the facial surface of the teeth when the device is placed over the dental arch. As used herein, an "axis" of the device includes both linear and curvilinear lines running from side edge to side edge of the device. FIG. 4 is a back view of the device of FIGS. 1 and 2, showing how folding of the device along the offset main fold line 150 and secondary fold lines 160 and 161 provides divides the device into larger and smaller portions as described above.

Figure 5:
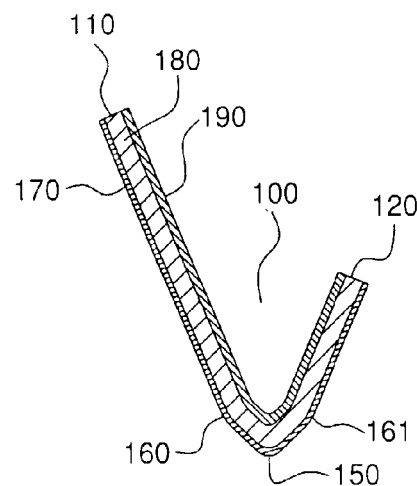
FIG. 5 is a cross-sectional view taken along line 3-3 of FIG. 3.

FIG. 5 is a cross-sectional view of the device 90 of FIGS. 1 and 2 along line 5-5 of FIG. 3, showing the arrangement of backing layer 170, anchor layer 180, and oral care layer 190. The device is bent along main fold line 150 and secondary fold lines 160 and 161 into a "reversed J" shape, so that the oral care layer 190 is located to the inside 100 of the device. The long arm of the "reversed J" ends in the front edge 110.

Figure 6:
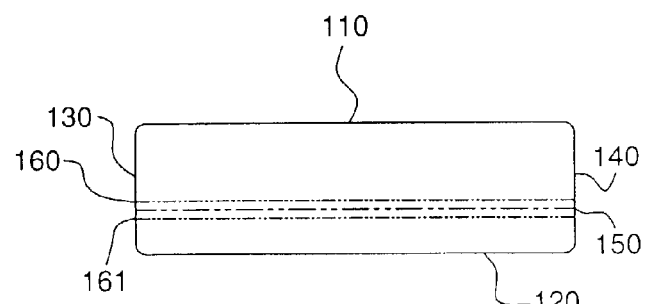
FIG. 6 is a top plan view of a flattened form of the device of FIG. 1.

FIG. 6 is a top plan view of the device of FIGS. 1 and 2 shown in flattened form to illustrate the rectangular shape of the unfolded device. Front edge 110 and back edge 120 are non-intersecting, and left side edge 130 and right side edge 140 are non-intersecting. Main fold line 150 and secondary fold lines 160 and 161 are located approximately ⅓ the distance from front edge 110 to back edge 120.

Figure 7:
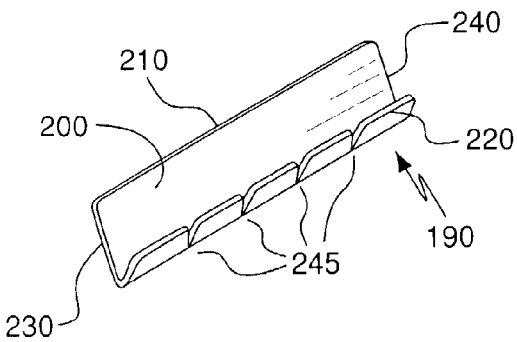
FIG. 7 is an isometric view of another embodiment of a device of the invention as seen from the back.

FIG. 7 is a back isometric view of another oral care delivery device of the invention generally designated 190, which is designed for placement over either the upper or lower dental arch. The inside 200 of the device, which is bounded by front edge 210, back edge 220, left side edge 230 and right side edge 240, contains the oral care layer. A plurality of notches 245 are spaced essentially evenly along the back edge 210 of the device. As described above, the notches help prevent buckling of the device when the device is formed over the curve of the dental arch. The device is substantially straight, and is molded to fit the curvature of the catenary arch during placement in the user's mouth.

Figure 8:
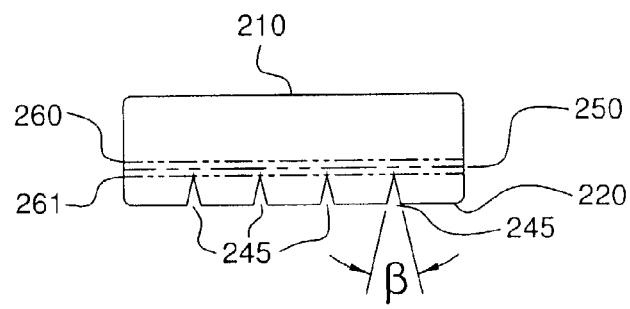
FIG. 8 is top plan view of a flattened form of the device of FIG. 7.

FIG. 8 shows the device 190 of FIG. 7 shown in flattened form to illustrate the rectangular shape of the unfolded device, and the positioning of notches 245. The device has a main fold line 250 and secondary fold lines 260 and 261 offset from front edge 210 as in the previous embodiment, located approximately ⅓ the distance from front edge 210 to back edge 220. The notches 245 extend from back edge 210 to the secondary fold 230 line closest to the back edge, with the apex of the notches contacting the secondary fold line. The sides of each notch form an angle β of approximately 28°.

Figure 9:
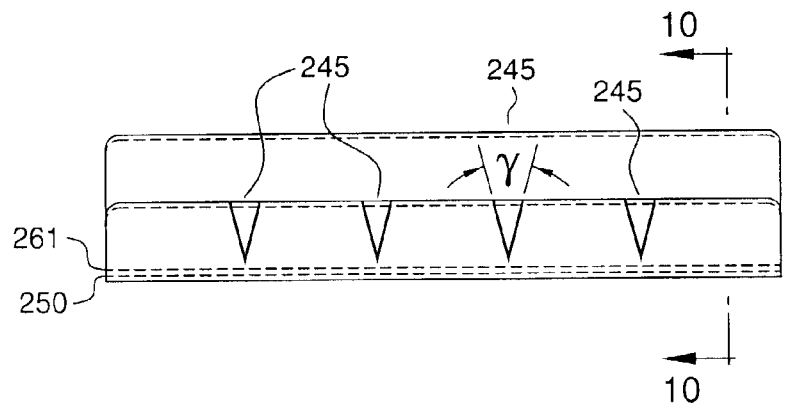
FIG. 9 is a back view of the device of FIG. 7.

FIG. 9 is a back view of the device 190 of FIG. 7, showing how folding of the device along the offset main fold line 250 and secondary fold lines 260 and 261 provides a portion of the device from the front edge to the fold lines which is larger than the portion from the back edge to the fold lines. The larger portion contacts with the facial surface of the teeth when the device is placed over the dental arch. The notches 245 are contained within the portion of the device which contacts the lingual surface of the teeth when placed over the dental arch. The sides of each notch form an angle γ of approximately 28°.

Figure 10:
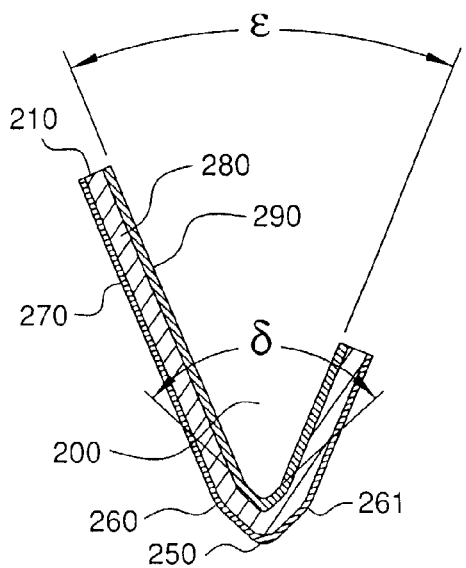
FIG. 10 is a cross-sectional view taken along line 9-9 of FIG. 9.

FIG. 10 is a cross-sectional view of the device 190 of FIG. 7 taken along line 10-10 of FIG. 9, showing the arrangement of backing layer 270, anchor layer 280, and oral care layer 290. The device is bent along main fold line 250 and secondary fold lines 260 and 261 into a "reversed J" shape, so that the oral care layer 290 is located to the inside 200 of the device. The long arm of the "reversed J" ends in the front edge 210. The surface of oral care layer 290 between the secondary fold lines 260 and 261 is bent into an angle δ of approximately 90° by folding the device along ε the main fold line 250. The surface of the oral care layer 290 between front edge 210 and the secondary fold line 260, and the surface of the oral care layer 290 between the back edge 220 and the secondary fold line 261, are bent into an angle ϵ of approximately 45° relative to each other by folding the device along each secondary fold line.

Figure 11:
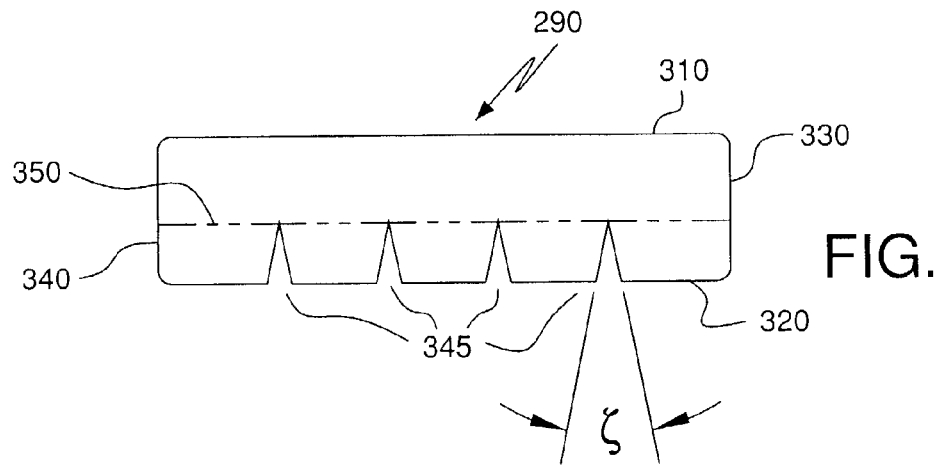
FIG. 11 is a top plan view of a flattened form of a further embodiment of a device of the invention.

FIG. 11 is a top plan view of a further oral care delivery device of the invention generally designated 290, which is designed to fit the upper dental arch of a user. The device is shown in flattened form to illustrate the rectangular shape. The rectangle is defined by front edge 310 and back edge 320, and side edges 330 and 340. The device has a single fold line 350 which is slightly offset from the center axis of the device toward the back edge 320. A plurality of substantially evenly spaced notches 345 are cut into back edge 320. The sides of each notch 345 form an angle ζ of approximately 22°, and the apex of each notch contacts fold line 350.

Figure 12:
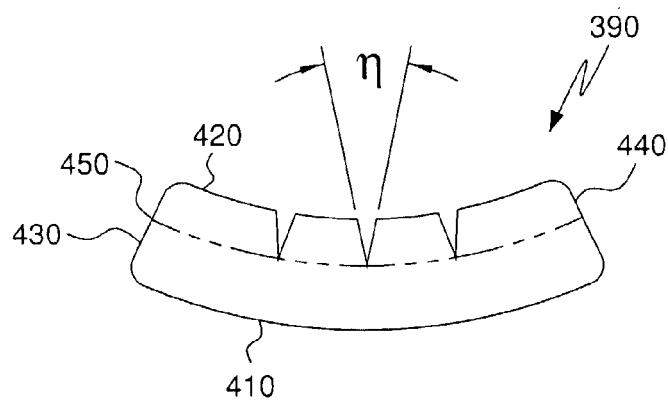
FIG. 12 is a top plan view of a flattened form of a further embodiment of a device of the invention.

FIG. 12 is a top plan view of another oral care delivery device of the invention generally designated 390, which is designed to fit the upper dental arch of a user. The device is shown in flattened form to illustrate the rectangular shape. The rectangle is defined by front edge 410 and back edge 420, and side edges 430 and 440. Front edge 410 and back edge 420 are curved in the same way and side edges 430 and 440 are slightly off-parallel. The device has a single fold line 450 which is slightly offset from the center axis of the device toward the back edge. A plurality of substantially evenly spaced notches 445 are cut into back edge 420. The sides of each notch 445 form an angle η of approximately 22°, and the apex of each notch contacts fold line 450.

Figure 13:
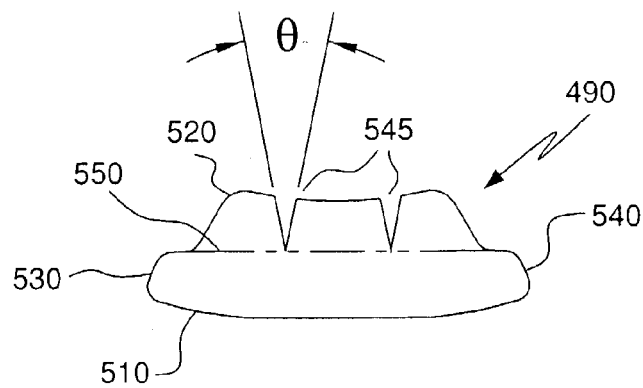
FIG. 13 is a top plan view of a flattened form of a further embodiment of a device of the invention.

FIG. 13 is a top plan view of a further oral care delivery device of the invention generally designated 490, which is designed to fit the lower dental arch of a user. The device is shown in flattened form to illustrate the essentially trapezoidal shape. The trapezoid is defined by front edge 510 and back edge 520, and side edges 530 and 540. Front edge 510 and back edge 520 are slightly curved, and back edge 520 is shorter in length than front edge 510. Side edges 530 and 540 are not straight, but follow an irregular course which forms protrusions on either side of the flattened pattern. When the device is folded and placed over the dental arch, the protrusions ensure that at least the facial surface of the incisors are in contact with the oral care layer. The device has a single fold line 550 which is slightly offset from the center of the device toward the back edge 520. A plurality of substantially evenly spaced notches 545 are cut into back edge 520. The sides of each notch 545 form an angle θ of approximately 22°, and the apex of each notch contacts fold line 550.

The device can be constructed using techniques well known in the art. For example, the components comprising the backing layer can be mixed, melted and extruded in a continuous or discontinuous layer of a desired thickness, which can be cut to the appropriate size and shape. Alternatively, the backing layer can be produced by pressing the mixed, melted components into a flat sheet of a desired thickness, which is then cut to the appropriate size and shape. The anchor layer can be attached to the backing layer by techniques well known in the art, such as lamination, hot-melt extrusion, and the like, or the two layers can be coextruded. A preferred method of attaching the anchor layer to the backing layer is pressing the anchor layer onto a heat-softened backing layer with slight pressure, for example as described in Example 1 below.

Likewise, the oral care layer can be prepared using polymer synthesis and formulation techniques known in the art (see, e.g., U.S. Pat. No. 4,581,821 of Cahalan et al., supra, and U.S. Published Application No. 2002/0037977 of Feldstein et al., supra), and formed into a layer of a desired thickness suitable for attachment to the anchor layer. For example, the polymers, plasticizers oral care agent and any other components comprising the oral care layer can be melted in a hotmelt mixer and extruded as a sheet between two release liners, or can be casted. The oral care layer can be removed from between the release liners and attached to the anchor layer; e.g., by lamination. Alternatively, the oral care layer can be extruded directly onto the anchor layer.

In one embodiment, an oral care agent, for example a hydrogen or carbamide peroxide, can be placed (e.g., by printing) on top of an anchor layer which has been attached to a backing layer. A melted mixture comprising all the components of an oral care layer except the oral care agent is then extruded directly on top of the oral care agent. As the melted oral care layer components solidify, the oral care agent is drawn into and distributed throughout the oral care layer.

Optionally, a scrim can be placed over the oral care agent which has been placed on top of an anchor layer, prior to extrusion of the oral care layer. The melted mixture comprising the remaining oral care layer components is then extruded onto the scrim, where it flows into and around the openings in the scrim so that the scrim is entirely surrounded by the melted oral care layer material. As the oral care layer solidifies, it absorbs the oral care agent as described above, and also entraps the scrim so that the scrim is embedded in the oral care layer.

Specific processes for constructing the devices of the invention are given in the Examples below.

Preferably, the device of the invention is provided to the user substantially ready for placement on the teeth. That is, the device will preferably be provided in substantially non-flat form, and all the user need do is conform the device onto the upper or lower dental arch with normal manual pressure.

In practice, the user wets the device before placement in the mouth, e.g., with water or saliva. Alternatively, the user can wet the surface of the teeth to be treated; e.g., with water or saliva, before placement of the device in the mouth. Wetting the device causes the hydrophilic polymer in the oral care layer to begin to swell, which in turn may enhance the adhesive properties of the layer and/or activate the oral care agent. Swelling of the hydrophilic polymer can also cause the oral care layer to fill in the cracks or irregularities found in the surface of the teeth and surrounding tissue, so that maximum contact is made with these surfaces.

The device is then placed over the teeth to be treated, and formed around the teeth and surrounding tissue with manual pressure. The device should be conformed to the teeth so that the oral care layer in substantially entirely in contact with at least the facial surfaces and the crowns of the teeth to be treated. Depending on the size of that portion of the device in contact with the lingual surface of the teeth to be treated, the lingual surface of the teeth may only be partially covered.

Once formed around the teeth and surrounding tissue, the device is left in place for a sufficient time to produce the desired effect. The length of time that the device should be left in place varies with the type of treatment to be performed, the severity of the condition, the age and health of the user, and the like. The length of time which the device is left on the teeth can therefore be varied in order to achieve a desired result. For both therapeutic and cosmetic applications, the device can be left in place, for example, for about 15 minutes to about 4 hours per treatment, preferably for about 30 minutes to about 1 hour per treatment. Longer and shorter treatment times are contemplated.

For embodiments of the invention which employ an oral care layer capable of sustained release of the oral care agent, treatment times can be substantially less than treatment times normally recommended for prior delivery systems. For example, treatment times of about 15 to about 30 minutes with a device of the invention employing a sustained release layer can produce results comparable to or better than those achieved with prior delivery systems using longer treatment times. Once a single treatment has been completed, the device is simply removed from the teeth by the user and discarded.

The frequency and total number of therapeutic or cosmetic treatments also depend on factors such as the type of treatment to be performed, the severity of the condition, the age and health of the user, and the like. The frequency and total number of treatments with the present device can therefore be varied in order to achieve a desired result. For therapeutic and cosmetic applications, the device can be applied to the teeth once or twice a day for 7 to 28 days, with the treatment regimen being repeated in 4 to 6 months from the last treatment.

For embodiments of the invention which employ an oral care layer capable of sustained release of the oral care agent, the frequency and total number of treatments can be substantially less than those recommended for prior delivery systems. For example, a device employing a sustained release oral care layer can be used once a day for 4 days to 2 weeks, with results comparable to or better than those achieved with prior delivery systems.

A preferred use of the device of the invention is to deliver a tooth whitening agent to the teeth. In practice, a device comprising an oral care layer which comprises a tooth whitening agent is provided to the use and is used as described above. Preferably, wetting the device activates the tooth whitening agent.

The device is left in place for a sufficient time to produce the desired effect. The length of time that the device should be left in place varies with the extent of the tooth discoloration or staining, the degree of whitening desired by the user, and the like. The length of time which the device is left on the teeth can therefore be varied in order to achieve a desired result. Generally, the device can be left in place for about 15 minutes to about 2 hours per treatment, preferably for about 30 minutes to about 1 hour per treatment. Longer and shorter treatment times are contemplated. A preferred treatment time is approximately 1 hour.

In a preferred embodiment, the device comprises an oral care layer capable of sustained release of the tooth whitening agent. In particular, the oral care layer can comprise a PEG-PVP-based pressure sensitive adhesive as disclosed in U.S. Published Application No. 2002/0037977 of Feldstein et al, supra. Use of sustained-release oral care layers can significantly reduce treatment times as compared to the treatment times normally recommended for prior tooth whitening systems.

After a single treatment has been completed, the device is removed from the teeth by the user and discarded. The treatment is preferably repeated once a day (using a fresh device for each treatment) for one to two weeks. More preferably, the tooth whitening treatment is repeated once a day for 4 to 7 days. The tooth whitening treatment regimen can be repeated after, for example, 4 to 6 months, depending on the extent to which tooth discoloration or staining occurs during this period.

The device of the invention can be packaged by any means suitable for containing and transporting the devices to the consumer. Preferably, the device is placed in a hermetically sealed, single use pouch. Preferably, these pouches are made of silicone or fluorocarbon coated foil, Mylar, or wax coated foil to protect the device. The device can be sealed within the pouch under full or partial vacuum. A preferred pouch design is of the "peel-n-seal" type, wherein the user is presented with the device upon opening the pouch. The user may then grasp the device only by the backing layer, thus minimizing the chance of damaging or contaminating the oral care layer.

It is contemplated that a plurality of devices in single use packages can be packaged together. For example, a number of devices in single use packages equal to the recommended number of treatments for a given treatment regimen can be provided to the consumer in a larger package.

The invention will now be illustrated with the following non-limiting examples.

Example 1

Construction of a Device for Delivering a Tooth Whitening Agent

A delivery system for delivering a tooth whitening agent according to the present invention was constructed as follows.

TABLE 3

Backing Layer Formulation

| Item | Brand Name | Supplier | Percentage |
|---|---|---|---|
| Microcrystalline Wax | Microcrystalline 180/185 | Koster Keunen Inc. | 50% |
| Paraffin Wax | Paraffin 140/145 | Koster Keunen Inc. | 15% |
| Hydrocarbon Resin | Escorez 5380 | ExxonMobil Chemical | 35% |

The backing layer was prepared as follows:

The microcrystalline wax, paraffin, and Escorez 5380 were weighed and transferred into a Qorpak® jar (Qorpak, Bridgeville, Pa.). The materials were heated to 85° C.-90° C. with stirring to obtain a clear liquid melt. The clear liquid melt was cooled 65° C.-75° C. with stirring. At this temperature, the viscosity of the clear liquid melt is such that a Gardner's knife can be used to make "draw-downs." A silicone-coated PET release liner (Rexam 92A; Rexam Coated Films & Papers, Charlotte, N.C.) was placed on a glass plate which had been heated to 38° C.-40° C. The clear liquid melt (at 65° C.-75° C.) was coated onto the release liner at thickness of about 0.64 mm (25 mils) using a Gardner's knife. Immediately after drawing down the clear liquid melt onto the release liner, the release liner with the clear liquid melt was removed from the warm glass plate and was cooled to room-temperature. The clear liquid melt solidified to form the backing layer. The target thickness for the backing layer is about 0.38 mm (15±2 mils); this process produced backing layers having a thickness of from about 0.25 mm-0.38 mm (10-15 mils).

Anchor Layer—The anchor layer was composed of an about 0.64 mm (25 mil) thick layer of reticulated, open cell, ether-based polyurethane foam (#40320303, LC16035AO) from Foamex International, Inc. (Linwood, Pa.), which was colored blue. The anchor layer was attached to the backing layer as follows:

The solidified backing layer on the release liner produced above was placed, release liner-side down, on a glass plate and heated to 65°-70° C. The polyurethane foam was placed on the backing layer, and a second release liner was placed on the foam, with the siliconized side of the release liner facing the foam. A roller was passed over this second release liner with slight pressure. The resultant set (first release liner/backing layer/foam/second release liner) was cooled to room temperature to form the backing layer/anchor layer laminate. The thickness of the backing layer/anchor layer laminate was about 0.8 mm (30±2 mils).

TABLE 4

Oral Cure Layer Formulation

| Item | Brand Name | Supplier | Percentage |
|---|---|---|---|
| Polyvinylpyrrolidone K90 (PVP90) | Kollidone 90 | BASF | 58% |
| Polyethylene Glycol 400 | Carbowax Polyethylene Glycol 400 | Union Carbide | 30% |
| Acrylic acid esters | Eudragit L100/55 | Rohm America | 12% |

The oral care layer was produced as follows:

The Kollidone 90 and Eudragit L100/55 powders were mixed and blended with the polyethylene glycol 400 using a hotmelt-mixing procedure at 140° C. in a standard hotmelt mixer-extruder. The blend was extruded at 140° C. through a slot die spaced at 0.25 mm (10 mils) width using a single screw extruder, to obtain a film of about 0.38 mm (15 mils) thick. The extrudate was collected on a siliconized release liner using standard post-extrusion collecting equipment.

The oral care agent (an aqueous hydrogen peroxide solution) was added to the oral care layer, and the oral care layer was laminated to the anchor layer, as follows:

A 35-50% hydrogen peroxide solution was printed onto the foam side of the backing layer/anchor layer laminate in a controlled process, such that the amount of hydrogen peroxide solution printed onto the foam was equivalent to 3-10% of oral care layer. The melted Kollidone 90-Eudragit L100/55-polyethylene glycol 400 blend was extruded on top of the hydrogen peroxide solution printed onto the anchor layer. The melted blend absorbed the hydrogen peroxide solution as it cooled, and in the process adhered itself to the foam anchor layer.

In some devices, a scrim was embedded in the oral care layer as follows.

DELNET® non-woven polyolefin fabric scrim was obtained from DelStar Technologies, Inc. (Middletown, Del.), and was placed over the aqueous hydrogen peroxide solution which had been printed onto the anchor layer. The melted Kollidone 90-Eudragit L100/55-polyethylene glycol 400 blend was extruded on top of the scrim. The melted blend flowed through and around the voids in the scrim, so that the scrim was entirely surrounded by the melted blend. Upon cooling and solidification of the melted blend, the scrim was embedded within the oral care layer. The melted blend also absorbed the hydrogen peroxide solution as it cooled, and in the process adhered itself to the foam anchor layer.

After the backing, anchor and oral care layers were formed as described above, devices of the invention were cut to the desired size and shape and vacuum formed on a forming die.

Example 2

Stability of the Tooth Whitening Agent.

Accelerated $H_2O_2$ stability studies were conducted at 40° C./75% relative humidity (RH) with the individual ingredients used to form the backing, anchor and oral care layers as described in Example 1. As shown in Table 5, the $H_2O_2$ showed good stability for up to 9 weeks under these conditions.

TABLE 5

Stability of $H_2O_2$
Hydrogen Peroxide Degradation (wt %)

| Individual Components | 40° C./75% RH | Time (weeks) |
|---|---|---|
| Polyvinylpyrrolidone K90 | 8.1 | 9 |
| Polyethylene Glycol 400 | 6.6 | 9 |
| Eudragit L100/55 | 8.0 | 5 |
| blended backing layer components | 9.8 | 9 |
| Polyurethane Foam | 2.7 | 9 |

Example 3

Efficacy of Tooth Whitening Treatments

The teeth whitening efficacy of the present devices was evaluated as follows.

A single subject used a device of the invention prepared as in Example 1 (containing 6% H2O2 and no scrim) on the lower dental arch once a day for 6 days. The duration of each treatment was approximately1 hour, except for the last treatment day (day 6), on which the device was worn for approximately 30 minutes. The shade of the subject's treated teeth was measured using the Professional Tooth Shade Guide before and after the device was worn on each treatment day. Photographs of subject's teeth were also taken immediately before and after the device was worn on each treatment day. The results of the test are given in Table 6.

TABLE 6

Results of Efficacy Study

| Day | Teeth Shade Before | Teeth Shade After |
|---|---|---|
| 1 | 12 | 10 |
| 2 | 10 | 8 |
| 3 | 7 | 5 |
| 4 | 6 | 4/5 |
| 5 | 4/5 | 2/3 |
| 6 | 2/3 | 2 |

Example 4

Rate of Delivery of Tooth Whitening Agent from the Oral Care Layer.

The rate of $H_2O_2$ release in vitro for devices of the invention made as in Example 1 was evaluated and compared to the in vitro $H_2O_2$ release rate for Crest whitestrips™ (lot#1298BT3B, Nov. 19, 2002, The Procter & Gamble Co., Cincinnati, Ohio). Crest Whitestrips™ (hereinafter "Whitestrips") are a commercially available tooth whitening system, which have 6% hydrogen peroxide in a Carbopol 956 gel on a thin polyethylene film.

The in vitro release of $H_2O_2$ from Whitestrips (containing approximately 6% $H_2O_2$) and from the present devices (containing approximately 3%, 6% or 9% $H_2O_2$) was measured through filter paper by standard techniques. In case of Whitestrips, peroxide levels dropped and the whitening efficiency decreased after 30 minutes (see FIG. 14). The data obtained for the Whitestrips is equivalent to published data (see Sagel P A, et al. (2000), Vital Tooth Whitening With a Novel Hydrogen Peroxide Strip System: Design, Kinetics, and Clinical Response. Compendium, Suppl. 29, Vol. 21: S10-S15, the entire disclosure of which is herein incorporated by reference.

Figure 14:
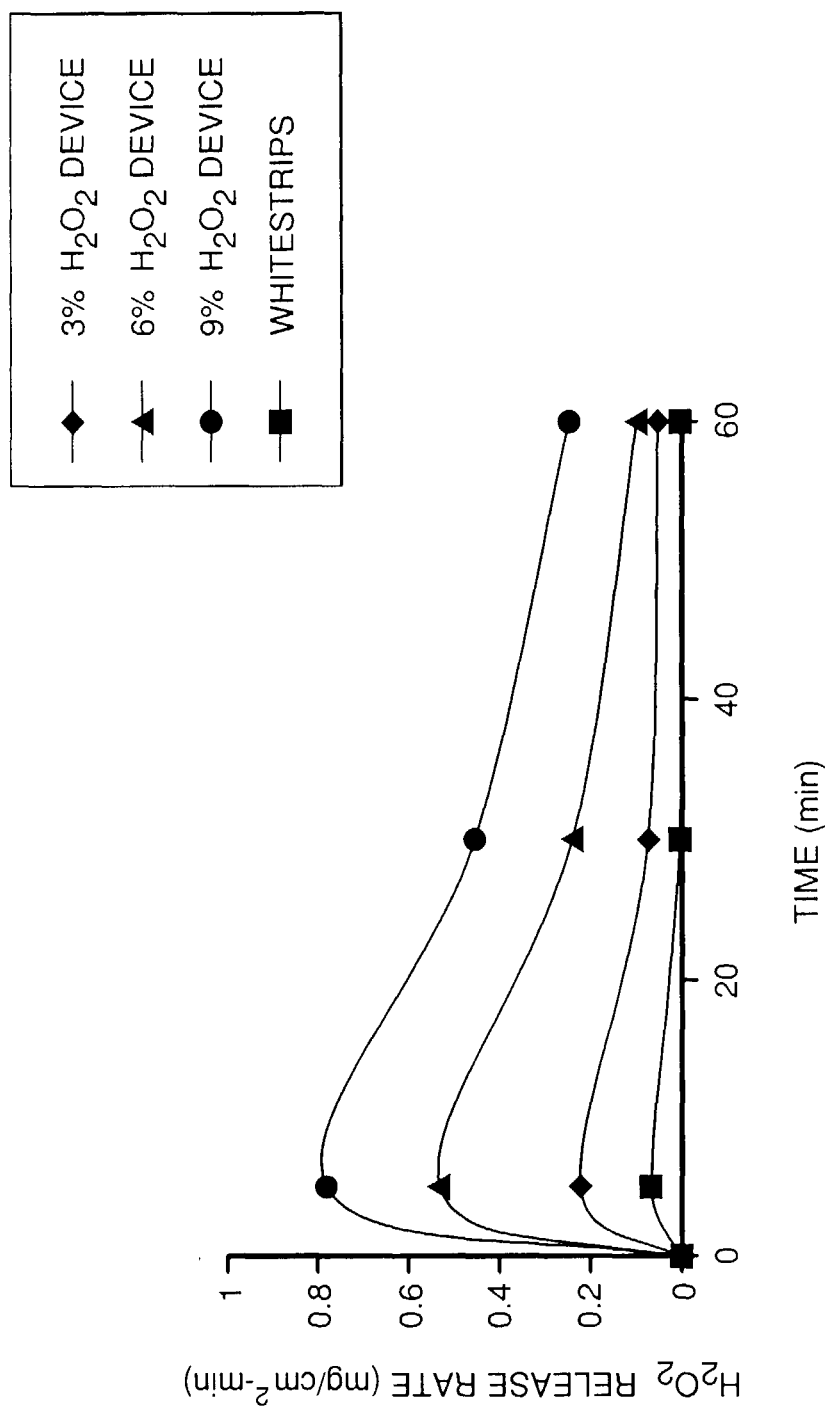
FIG. 14 is a plot of the in vitro $H_2O_2$ release rate (in mg/cm$^2$-min.) vs. time (in minutes) for devices of the invention having approximately 3% $H_2O_2$ ("3% $H_2O_2$ Device"); approximately 6% $H_2O_2$ ("6% $H_2O_2$ Device"); approximately 9% $H_2O_2$ ("9% $H_2O_2$ Device"); and Crest Whitestrips ("Whitestrips").

The devices of the present invention released $H_2O_2$ at a higher rate than the Whitestrips through 30 minutes and up to the 60 minute time-limit of the study (see FIG. 14). The $H_2O_2$ release rate for the device containing ~6% $H_2O_2$ (which has an $H_2O_2$ concentration comparable to the Whitestrips) at 5, 30 and 60 minutes was approximately 7.5-, 24- and 10-fold higher, respectively, than the $H_2O_2$ release rate from the Whitestrips for the same time points. The $H_2O_2$ release rate for the device containing ~3% $H_2O_2$ at 5, 30 and 60 minutes was approximately 3-, 7- and 5-fold higher, respectively, as compared to the Whitestrips at the same time points. The data used to produce the plot of FIG. 14 is given in Table 7 below.

TABLE 7

| Time (min) | $H_2O_2$ remaining (mg) | $H_2O_2$ Delivery Rate (mg/cm$^2$-min) |
|---|---|---|
| 3% $H_2O_2$ Device | | |
| 0 | 39.50 | 0 |
| 5 | 34.56 | 0.22 |
| 30 | 26.33 | 0.07 |
| 60 | 19.11 | 0.05 |
| 6% $H_2O_2$ Device | | |
| 0 | 87.2 | 0 |
| 5 | 75.38 | 0.53 |
| 30 | 48.77 | 0.24 |
| 60 | 35.47 | 0.10 |
| 9% $H_2O_2$ Device | | |
| 0 | 141.70 | 0 |
| 5 | 124.38 | 0.78 |
| 30 | 74.00 | 0.45 |
| 60 | 40.94 | 0.25 |
| Crest Whitestrips ™: Lot 1298BT3B (Nov. 19, 2002) | | |
| 0 | 8.30 | 0 |
| 5 | 5.72 | 0.07 |
| 30 | 4.58 | 0.01 |
| 60 | 3.43 | 0.01 |

Example 5

Toxicity Study

Regulatory agencies occasionally require testing to demonstrate the potential irritancy of a substance on mucous membrane. A review of available literature does not indicate currently acceptable in vitro testing alternatives. In order to reasonably evaluate the potential for mucous membrane irritancy in humans, a mammalian in vivo system is necessary.

Hamsters were selected as the model, since they are accepted as a standard by regulatory agencies in oral mucosal irritancy testing. Additionally, previous studies by others have shown that the hamster model is more sensitive and predictive of potential human oral mucosa irritancy than other species.

Therefore, a toxicity test was conducted on a device of the invention prepared as in Example 1 (containing 6% H2O2 and no scrim), using Syrian Golden Hamsters according to Protocol Number X2E228G, which incorporates by reference Northview Standard Operating Procedure 16G-39 and is itself herein incorporated by reference in its entirety. Protocol Number X2E228G is on file at Northview Pacific Laboratories, Inc. As described in more detail below, the toxicity test showed that the device of the invention was minimally irritating to the mucosa in Syrian Golden Hamsters, and is thus expected to be safe for use in humans.

Three Syrian Golden hamsters were used for the toxicity test. In order to immobilize the animals, to facilitate scoring and dosing, each hamster was first anesthetized with 0.02 to 0.03 ml of a ketamine/sylazine/acepromazine solution injected into the thigh muscle. At this dose level, the animals were relaxed but not fully unconscious. Anesthesia preparation and use were according to NV SOP 16A-10, the entire disclosure of which is herein incorporated by reference.

After each animal was anesthetized, the right and left cheek pouches were everted, examined and visually scored. An approximately 1 cm$^2$ piece of the device (hereinafter the "patch") was inserted into the right cheek pouch. After dosing, a collar, fastened with Velcro, was placed around the animal's neck to prevent it from everting its cheek pouch or removing the patch. The left cheek pouch remained untreated as a control. One hour after dosing, the patch was removed from the right cheek pouch and the cheek pouch was visually scored. The patches were weighted on a precision analytical balance after removal. The dosing and scoring procedure was repeated four times over four hours, at one hour intervals. After the fourth dose, the patches were removed and the cheek pouches examined and visually scored one final time.

Twenty-four hours after the last dose, the animals were again examined and the cheek pouches visually scored. They were then euthanized with a 0.2 ml intraperitoneal injection of Euthasol. Pieces of the left and right cheek pouches were excised and placed in a separate cassettes, which were then placed in 10% buffered formalin and sent to IDEXX Veterinary Services, Inc., West Sacramento, Calif. for histological evaluation.

Clinical Observations

None of the animals showed signs of mortality, ill health, or reaction to treatment during the study. Also, no gross toxicity symptoms were observed in any of the animals.

Macroscopic Scoring

The macroscopic visual scoring of the cheek pouch tissue was done according to AAMI Standards and Recommended Practices, Vol. 4: Biological Evaluation of Medical Device (1997) pp. 265-268, the entire disclosure of which is herein incorporated by reference. The score for the treated right cheek pouch was compared to the left cheek pouch. An average score was determined for each animal by adding the reaction scores at each time point and dividing by the total number time points. A group score was determined by dividing the sum of the average individual scores by the number of animals tested. The untreated scores for the (left) cheek pouch were calculated separately. These scores are given in Table 8.

As shown in Table 8, very slight erythema was observed in the nine of the fifteen scorings of the treated pouch. This may have resulted from mechanical irritation occurring when the adhesive patch was pulled away from the mucosa.

TABLE 8

Macroscopic Assessment of Cheek Pouch Reaction Scores

| Animal Number | Before Dose 1 | | After Dose 1 | | After Dose 2 | | After Dose 3 | | After Dose 4 | | +24 Hours After Dose 4 | |
|---|---|---|---|---|---|---|---|---|---|---|---|---|
| | L | R | L | R | L | R | L | R | L | R | L | R |
| 83 | 1 | 0 | 0 | 1 | 0 | 0 | 0 | 0 | 0 | 0 | 0 | 1 |
| 87 | 0 | 0 | 0 | 1 | 0 | 1 | 0 | 1 | 0 | 1 | 0 | 1 |
| 91 | 0 | 0 | 0 | 0 | 0 | 1 | 0 | 0 | 0 | 1 | 0 | 0 |

TABLE 9

Histological Assessment of Oral Tissue

| Animal Number | Epithelium | Leukocytes | Congestion | Edema | | Total Animal Score |
|---|---|---|---|---|---|---|
| Test Pouch (Right cheek) | | | | | | |
| 83 | 0 | 1 | 0 | 0 | | 1 |
| 87 | 0 | 1 | 0 | 2 | | 3 |
| 91 | 0 | 1 | 0 | 0 | | 1 |
| | | | | | Total: | 5 |
| | | | | | Average: | 2 |
| Control Pouch (Left cheek) | | | | | | |
| 83 | 0 | 0 | 0 | 0 | | 0 |
| 87 | 0 | 0 | 0 | 0 | | 0 |
| 91 | 0 | 1 | 0 | 0 | | 1 |
| | | | | | Total: | 1 |
| | | | | | Average: | 0 |

Oral Irritation Index + $T_{average} - C_{average}$ = 2 (Minimally Irritating)
T = Test
C = Control Microscopic Histology Microscopic histological evaluation of the tissue was conducted by a Board-certified veterinary pathologist. The pathologist scored each tissue and described the potential for oral irritation according to the AAMI Standards and Recommended Practices (1997), supra. The scores for microscopic evaluation of the right (test) cheek pouch for all animals in the test group were added and divided by the number of observations to obtain a test group average. The process was repeated for the left (control) cheek pouch. The maximum score is 16. A total microscopic evaluation score greater than 9 for the control cheek pouch may indicate underlying pathology. The control cheek pouch average was subtracted from the test group average to obtain the Oral Irritation Index. A description rating was given for each set of reactions, based on the Oral Irritation Index. These results are presented in Table 9.

As shown in Table 9, the oral irritation index for the right cheek pouches was 2 (minimal irritation), and the average score for the untreated pouch was 0 (no irritation).

Based on the results of the toxicity test, the device of the invention was deemed minimally irritating to the mucosa in Syrian Golden Hamsters, and therefore is considered safe for use in humans.

All documents referred to herein are incorporated by reference. While the present invention has been described in connection with the preferred embodiments and the various figures, it is to be understood that other similar embodiments may be used or modifications and additions made to the described embodiments for performing the same function of the present invention without deviating therefrom. Therefore, the present invention should not be limited to any single embodiment, but rather should be construed in breadth and scope in accordance with the recitation of the appended claims.

We claim:

1. A device for delivering an oral care agent, wherein the device is sized to fit over a plurality of teeth in an upper or lower dental arch in a subject, comprising:
    a permanently deformable backing layer;
    an anchor layer comprising a layer of an open-cell foam, the anchor layer having a first side and second side opposite said fist side, the first side in contact with the backing layer; and the backing layer penetrating into the first side of the anchor layer and
    an oral care layer comprising at least one oral care agent and at least one hydrophilic polymer, wherein the oral care layer is in contact with the second side of the anchor layer and forms an adhesive bond thereto,
    and wherein the oral care layer is minimally invested in the anchor layer and has an adhesiveness when hydrated relative to the surface of a the teeth of user that is sufficient to retain the device on the user's teeth when placed thereon.

2. The device of claim 1, wherein the backing layer is from about 0.025 mm to about 2 mm thick.

3. The device of claim 1, wherein the backing layer is from about 0.125 to about 0.8 thick.

4. The device of claim 1, wherein the backing layer is about 0.75 mm thick.

5. The device of claim 1, wherein the backing layer comprises a non-polymeric material.

6. The device of claim 1, wherein the non-polymeric material comprises a wax, a resin, or mixtures thereof.

7. The device of claim 6, wherein the wax is selected from the group consisting of a microcrystalline wax; a paraffin wax; a synthetic paraffin wax; and mixtures thereof.

8. The device of claim 6, wherein the resin is a hydrocarbon resin.

9. The device of claim 8, wherein the hydrocarbon resin is a water-white, clear cycloaliphatic hydrocarbon resin.

10. The device of claim 1 wherein the backing layer is colored.

11. The device of claim 10 wherein the backing layer is colored with at least one colorizing compound.

12. The device of claim 11 wherein the at least one colorizing compound is selected from the group consisting of FD&C Red No. 3; Food Red 17; Food Yellow 13; FD&C Yellow No. 5; FD&C Yellow No. 6; FD&C Green No. 3; FD&C Blue No. 1; FD&C Blue No. 2; FD&C Red No. 40; Orange B; Citrus Red No. 2; and combinations thereof.

13. The device of claim 11 wherein the at least one colorizing compound is selected from the group consisting of annatto extract; beta-apo-8'-carotenal; beta-carotene; beet powder; canthaxanthin; caramel color; carrot oil; cochineal extract (carmine); toasted, partially defatted, cooked cottonseed flour; ferrous gluconate; fruit juice; grape color extract; grape skin extract (enocianina); paprika; paprika oleoresin; riboflavin; saffron; turmeric; turmeric oleoresin; vegetable juice; and combinations thereof.

14. The device of claim 12 wherein the at least one colorizing compound is selected from the group consisting of titanium dioxide; chromium oxide greens; ultramarine blues and pinks; and ferric oxides.

15. The device of claim 11, wherein the dye comprises a dye-lake form.

16. The device of claim 15, wherein the dye-lake form is selected from the group consisting of FD&C Green #1 lake; FD&C Blue #2 lake; FD&C R&D #30 lake; and FD&C Yellow #15 lake.

17. The device of claim 11, wherein the at least one colorizing compound comprises about 0.05% to about 10% by weight of the backing layer.

18. The device of claim 17, wherein the at least one colorizing compound comprises about 0.1% to about 5% by weight of the backing layer.

19. The device of claim 11, wherein the backing layer comprises multiple colors.

20. The device of claim 19, wherein the multiple colors comprise a pattern.

21. The device of claim 11, wherein the backing layer further comprises glitter particles.

22. The device of claim 1, wherein the backing layer is embedded or decorated with decorative items.

23. The device of claim 11, wherein the backing layer is embedded or decorated with decorative items.

24. The device of claim 1, wherein the backing layer displays letters, words, or images.

25. The device of claim 11, wherein the backing layer displays letters, words, or images.

26. The device of claim 1, wherein the open-cell foam comprises a polyurethane, polystyrene or polyethylene foam.

27. The device of claim 26, wherein the open-cell foam comprises an ether based reticulated polyurethane foam.

28. The device of claim 1, wherein the anchor layer is from about 0.025 mm to about 1 mm thick.

29. The device of claim 28, wherein the anchor layer is about 0.6 mm to about 0.8 mm thick.

30. The device of claim 1, wherein the anchor layer is colored.

31. The device of claim 30 wherein the anchor layer is colored with at least one colorizing compound.

32. The device of claim 31 wherein the at least one colorizing compound is selected from the group consisting of FD&C Red No. 3; Food Red 17; Food Yellow 13; FD&C Yellow No. 5; FD&C Yellow No. 6; FD&C Green No. 3; FD&C Blue No. 1; FD&C Blue No. 2; FD&C Red No. 40; Orange B; Citrus Red No. 2; and combinations thereof.

33. The device of claim 31 wherein the at least one colorizing compound is selected from the group consisting of annatto extract; beta-apo-8'-carotenal; beta-carotene; beet powder; canthaxanthin; caramel color; carrot oil; cochineal extract (carmine); toasted, partially defatted, cooked cottonseed flour; ferrous gluconate; fruit juice; grape color extract; grape skin extract (enocianina); paprika; paprika oleoresin; riboflavin; saffron; turmeric; turmeric oleoresin; vegetable juice; and combinations thereof.

34. The device of claim 31 wherein the at least one colorizing compound is selected from the group consisting of titanium dioxide; chromium oxide greens; ultramarine blues and pinks; and ferric oxides.

35. The device of claim 31, wherein the dye comprises a dye-lake form.

36. The device of claim 35, wherein the dye-lake form is selected from the group consisting of FD&C Green #1 lake; FD&C Blue #2 lake; FD&C R&D #30 lake; and FD&C Yellow #15 lake.

37. The device of claim 31, wherein the colorizing compound comprises about 0.05 percent to about 10 percent by weight of the anchor layer.

38. The device of claim 37, wherein the colorizing compound comprises about 0.1 percent to about 5 percent by weight of the anchor layer.

39. The device of claim 31, wherein the anchor layer comprises multiple colors.

40. The device of claim 1, wherein the oral care layer is from about 0.025 mm to about 4 mm thick.

41. The device of claim 40, wherein the oral care layer is from about 0.125 mm to about 1.5 mm thick.

42. The device of claim 41, wherein the oral care layer is from about 0.25 mm to about 1.0 mm thick.

43. The device of claim 42, wherein the oral care layer is about 0.3 mm thick.

44. The device of claim 1, wherein the adhesiveness of the oral care layer with respect to the surface of the user's teeth is from about 200 N/m to about 400 N/m.

45. The device of claim 1, wherein the at least one oral care agent is entrapped within the oral care layer.

46. The device of claim 45, wherein the at least one oral care agent is released from the hydrophilic polymer upon hydration of the oral care layer.

47. The device of claim 1, wherein the at least one oral care agent is activated upon hydration of the oral care layer.

48. The device of claim 1 wherein the oral care layer comprises a pressure-sensitive adhesive comprising at least one oral care agent, at least one hydrophilic polymer, and at least one water-soluble plasticizer that is miscible with the hydrophilic polymer.

49. The device of claim 48 wherein the at least one hydrophilic polymer has a hydrophilicity as measured by water uptake of greater than about 25%.

50. The device of claim 49 wherein the at least one hydrophilic polymer has a glass transition temperature T(g) or melting point T(m) higher than about 25° C. and lower than about 120° C.

51. The device of claim 50, wherein the at least one hydrophilic polymer has a glass transition temperature T(g) or melting point T(m) higher than about 30° C. and lower than about 100° C.

52. The device of claim 48 wherein the at least one hydrophilic polymer is selected from the group consisting of polysaccharides; water-soluble synthetic polymers; polypeptides; and natural gums.

53. The device of claim 48 wherein the at least one hydrophilic polymer is selected from the group consisting of starches and starch derivatives; polyvinyl pyrrolidone; polyvinyl alcohol; hydroxypropyl cellulose; sodium carboxymethyl cellulose; polyethylene oxide; polyacrylic acid; polyacrylates; carboxylic acid polymers; xanthan gum; karaya gum; and gelatin.

54. The device of claim 48 wherein the at least one plasticizer is liquid at room temperature and has a boiling point higher than about 80° C.

55. The device of claim 54 wherein the at least one plasticizer is selected from the group consisting of glycerins; sorbitol; glycols; polysorbate 80; triethyl titrate; acetyl triethyl titrate; and tributyl titrate.

56. The device of claim 48, wherein the oral care layer comprises at least one crosslinked or non-crosslinked polymer selected from the group consisting of 2-acrylamido-2- methyl-propanesulfonic acid; polyvinyl pyrrolidone; polyethylene oxide; acrylates; polyvinyl alcohol; and carboxylic acid polymers.

57. The device of claim 56, wherein the oral care layer comprises crosslinked or non-crosslinked 2-acrylamido-2-methyl-propanesulfonic acid.

58. The device of claim 56, wherein the oral care layer comprises crosslinked or non-crosslinked polyvinyl pyrrolidone.

59. The device of claim 1, wherein the oral care layer is a sustained release oral care layer.

60. The device of claim 48, wherein the oral care layer is a sustained release oral care layer.

61. The device of claim 58, wherein the oral care layer is a sustained release oral care layer.

62. The device of claim 61 wherein the sustained-release oral care layer releases the at least one oral care agent at a rate of approximately 0.2 mg/cm$^2$-min to 1 mg/cm$^2$-min.

63. The device of claim 1, wherein the amount of the at least one oral care agent in the oral care layer is about 0.01% to about 40%.

64. The device of claim 63, wherein the amount of the at least one oral care agent in the oral care layer is about 0.1% to about 20%.

65. The device of claim 64, wherein the amount of the at least, one oral care agent in the oral care layer is about 0.5% to about 10%.

66. The device of claim 65, wherein the amount of the at least one oral care agent in the oral care layer is about 1% to about 7%.

67. The device of claim 1, wherein the at least one oral care agent is a pharmaceutically active agent or a cosmetically active agent.

68. The device of claim 67, wherein the pharmaceutically active agent is selected from the group consisting of a non-steroidal anti-inflammatory/analgesic; a steroidal anti-inflammatory agent; a local anesthetic; a bactericide/disinfectant; an antibiotic; an antifungal; a tooth desensitizing agent; a fluoride anticavity/antidecay agent; an anti tartar/anti-calculus agent; an enzyme which inhibits the formation of plaque, calculus or dental caries; and a nutritional supplement for local delivery to the teeth and surrounding tissue.

69. The device of claim 68, wherein the non-steroidal anti-inflammatory/analgesic agent is selected from the group consisting of acetaminophen; methyl salicylate; monoglycol salicylate; aspirin; mefenamic acid; flufenamic acid; indomethacin; diclofenac; alclofenac; diclofenac sodium; ibuprofen; flurbiprofen; fentizac; bufexamac; piroxicam; phenylbutazone; oxyphenbutazone; clofezone; pentazocine; mepirizole; and tiaramide hydrochloride.

70. The device of claim 68, wherein the steroidal anti-inflammatory agent is selected from the group consisting of include hydrocortisone; prednisolone; dexamethasone; triamcinolone acetonide; fluocinolone acetonide; hydrocortisone acetate; prednisolone acetate; methylprednisolone; dexamethasone acetate; betamethasone; betamethasone valerate; flumetasone; flourometholone; budesonide; and beclomethasone dipropionate.

71. The device of claim 68, wherein the local anesthetic is selected from the group consisting of dibucaine hydrochloride; dibucaine; lidocaine hydrochloride; lidocaine; benzocaine; p-buthylaminobenzoic acid 2-(diethylamino)ethyl ester hydrochloride; procaine hydrochloride; tetracaine hydrochloride; chloroprocaine hydrochloride; oxyprocaine hydrochloride; mepivacaine; cocaine hydrochloride; and piperocaine hydrochloride.

72. The device of claim 68, wherein the bactericide/disinfectant is selected from the group consisting of thimerosol; phenol; thymol; benzalkonium chloride; benzethonium chloride; chlorhexidine; providone iodide; cetylpyridinium chloride; eugenol, and trimethylammonium bromide.

73. The device of claim 68, wherein the antibiotic is selected from the group consisting of penicillin; meticillin; oxacillin; cefalotin; cefaloridin; erythromycin; lincomycin; tetracycline; chlortetracycline; oxytetracycline; metacycline; chloramphenicol; kanamycin; streptomycin; gentamicin; bacitracin; and cycloserine.

74. The device of claim 68, wherein the antifungal drug is selected from the group consisting of amphotericin; clotrimazole; econazole nitrate; fluconazole; griseofulvin; itraconazole; ketoconazole; miconazole; nystatin; terbinafine hydrochloride; undecenoic acid; and zinc undecenoate.

75. The device of claim 68, wherein the tooth-desensitizing agent is selected from the group consisting of potassium nitrate and strontium chloride.

76. The device of claim 68, wherein the fluoride anticavity/antidecay agent is selected from the group consisting of sodium fluoride, potassium fluoride and ammonium fluoride.

77. The device of claim 68, wherein the anti-tartar/anti-calculus agents is selected from the group consisting of phosphates; pyrophosphates, polyphosphates, polyphosphonates; linear carboxylic acids; sodium zinc citrate; and mixtures thereof.

78. The device of claim 68, wherein the enzyme which inhibits the formation of plaque, calculus or dental caries is selected from the group consisting of proteases; lipases; dextranases, glucanohydrolases, endoglycosidases, mucinases; amylases; and mixtures thereof.

79. The device of claim 68, wherein the nutritional supplement for local delivery to the teeth and surrounding tissue is a vitamin or mineral.

80. The device of claim 79, wherein the nutritional supplement for local delivery to the teeth and surrounding tissue is a vitamin selected from the group consisting of vitamin C; vitamin D; thiamine; riboflavin; calcium pantothenate; niacin; folic acid; nicotinamide; pyridoxine; cyanocobalamin; para-aminobenzoic acid; bioflavonoids; and mixtures thereof.

81. The device of claim 79, wherein the nutritional supplement for local delivery to the teeth and surrounding tissue is a mineral selected from the group consisting of calcium; phosphorus; fluoride; zinc; manganese; potassium; and mixtures thereof.

82. The device of claim 67, wherein the cosmetically active agent is selected from the group consisting of a breath freshener; a tooth whitening agent; and a tooth coloring or tinting agent.

83. The device of claim 82, wherein the tooth whitening agent is selected from the group consisting of peroxides; metal chlorites; perborates; percarbonates; peroxyacids; and combinations thereof.

84. The device of claim 83, wherein the tooth whitening agent is a peroxide selected from the group consisting of hydrogen peroxide; calcium peroxide; carbamide peroxide; and mixtures thereof.

85. The device of claim 83, wherein the tooth whitening agent is a metal chlorite selected from the group consisting of calcium chlorite; barium chlorite; magnesium chlorite; lithium chlorite; sodium chlorite; and potassium chlorite; hypochlorite and chlorine dioxide.

86. The device of claim 83, wherein the concentration of tooth whitening agent in the oral care layer is about 0.01% to about 40%.

87. The device of claim 84, wherein the peroxide compound in the oral care layer is equivalent to about 0.1% to about 20% hydrogen peroxide.

88. The device of claim 87, wherein the peroxide compound in the oral care layer is equivalent to about 0.5% to about 10% hydrogen peroxide.

89. The device of claim 88, wherein the peroxide compound in the oral care layer is equivalent to about 1% to about 7% hydrogen peroxide.

90. The device of claim 89, wherein the peroxide compound in the oral care layer is equivalent to about 6% hydrogen peroxide.

91. The device of claim 84, wherein the amount of hydrogen peroxide in the oral care layer is from about 0.1% to about 30%.

92. The device of claim 91, wherein the amount of hydrogen peroxide in the oral care layer is from about 3% to about 20%.

93. The device of claim 92, wherein the amount of hydrogen peroxide in the oral care layer is from about 6% to about 10%.

94. The device of claim 1, wherein the oral care layer further comprises a colorizing compound; food additive; flavorant; sweetener; or preservative.

95. The device of claim 94, wherein the flavorant is selected from the group consisting of wintergreen; peppermint; spearmint; menthol; fruit flavors; vanilla; cinnamon; spices; flavor oils; oleoresins; and mixtures thereof.

96. The device of claim 94, wherein the sweetener is selected from the group consisting of sucrose; fructose; aspartame; xylitol; and saccharine.

97. a device for delivering an oral care agent, wherein the device is sized to fit over a plurality of teeth in an upper or lower dental arch in a subject, comprising:
a permanently deformable backing layer, wherein the backing layer comprises 50% microcrystalline wax, 15% paraffin wax; and 35% hydrocarbon resin;
an anchor layer having a first side and second side opposite said first side, the first side in contact with the backing layer the anchor layer comprises an ether based reticulated open cell polyurethane foam; and
an oral care layer comprises at least one oral care agent and at least one hydrophilic polymer, wherein the oral care layer is in contact with the second side of the anchor layer and forms an adhesive bond thereto, wherein the oral care layer comprises 6% hydrogen peroxide, 58% polyvinylpyrrolidone K90, 33% polyethylene glycol 400; and 12% methacrylic acid—ethyl acrylate copolymer (1:1),
and wherein the oral care layer is minimally invested in the anchor layer and has an adhesiveness when hydrates relative to the surface of the teeth of the user that is sufficient to retain the device on the user's teeth when placed thereon.

98. The device of claim 97, wherein the anchor layer is colored.

99. The device of claim 1, further comprising a release liner or covering over the oral care layer.

100. The device of claim 1, further comprising a scrim embedded in the oral care layer.

101. The device of claim 97, further comprising a scrim embedded in the oral care layer.

102. The device of claim 101, wherein the scrim comprises woven, non-woven or perforated sheetlike materials.

103. The device of claim 102, wherein the woven materials are selected from the group consisting of cotton; a polyolefin; polyester; polyurethane; polyamide; polyaramide; and glass.

104. The device of claim 102, wherein the non-woven material is selected from the group consisting of felt; a polyolefin; polyester; polyurethane; polyamide; polyaramide; and glass.

105. The device of claim 102, wherein the perforated material comprises fine pitch polypropylene net.

106. The device of claim 100, wherein the scrim comprises a non-woven polyolefin.

107. The device of claim 101, wherein the scrim comprises a non-woven polyolefin.

108. The device of claim 1 which has a "J", "reversed J", "V", "U", or "C" shape when viewed in cross-section.

109. The device of claim 1 which is sized to fit the primary, mixed or permanent dentition of a human being.

110. The device of claim 1 which is of sufficient length and width to cover the facial surface, crowns and at least partially cover the lingual surface of the incisors in an upper or lower dental arch of a human being.

111. The device of claim 1 which is of sufficient length and width to cover the facial surface, crowns and at least partially cover the lingual surface of the anterior teeth in an upper or lower dental arch of a human being.

112. The device of claim 1 which is of sufficient length and width to cover the facial surface, crowns and at least partially cover the lingual surface of the anterior and posterior teeth in an upper or lower dental arch of a human being.

113. The device of claim 1 designed to fit the upper dental arch of a human being, wherein the device is about 7 cm to about 9 cm in length, and about 0.8 cm to about 2.5 cm in width.

114. The device of claim 1 designed to fit the lower dental arch of a human being, wherein the device is about 4 cm to about 6 cm in length, and about 1 cm to about 2 cm in width.

115. The device of claim 1, wherein the device, when viewed in plan view, is bent into an essentially horseshoe shape that generally matches the catenary arch of a human being.

116. The device of claim 1 further comprising one or more notches.

117. The device of claim 1, wherein the device is substantially non-flat.

118. A method for delivering an oral care agent to the teeth in an upper or lower dental arch in a subject, which teeth are in need of treatment, comprising:
1) providing the device of claim 1;
2) wetting the teeth or the oral care layer of the device;
3) placing the device over the teeth of a dental arch which are in need of treatment, and
4) conforming the device to the teeth and surrounding tissue by manual pressure so that the oral care layer is in contact with at least the facial surface of the teeth to be treated.

119. The method of claim 118, wherein the oral care layer comprises a pressure-sensitive adhesive comprising at least one oral care agent, at least one hydrophilic polymer, and at least one water-soluble plasticizer that is miscible with the hydrophilic polymer.

120. The method of claim 119, wherein the at least one hydrophilic polymer has a hydrophilicity as measured by water uptake of greater than about 25%.

121. The method of claim 120, wherein the at least one hydrophilic polymer has a glass transition temperature $T(g)$ or melting point $T(m)$ higher than about 25° C. and lower than about 120° C.

122. The method of claim 121, wherein the oral care layer comprises at least one crosslinked or non-crosslinked polymer selected from the group consisting of 2-acrylamido-2- methyl-propanesulfonic acid; polyvinyl pyrrolidone; polyethylene oxide; acrylates; polyvinyl alcohol; and carboxylic acid polymers.

123. The method of claim 122, wherein the oral care layer comprises crosslinked or non-crosslinked 2-acrylamido-2-methyl-propanesulfonic acid.

124. The method of claim 122, wherein the oral care layer comprises crosslinked or non-crosslinked polyvinyl pyrrolidone.

125. The method of claim 118, wherein the oral care layer is a sustained release oral care layer.

126. The method of claim 124, wherein the oral care layer is a sustained release oral care layer.

127. The method of claim 126, wherein the sustained-release oral care layer releases the at least one oral care agent at a rate of approximately 0.2 mg/cm$^2$-min to 1 mg/cm$^2$-min.

128. The method of claim 118, wherein the treatment comprises a cosmetic treatment.

129. The method of claim 118, wherein the device is left on the teeth for about 15 minutes to about 4 hours.

130. The method of claim 129, wherein the device is left on the teeth for about 30 minutes to about 1 hour.

131. A method for delivering a tooth whitening agent to the teeth in an upper or lower dental arch in a subject comprising:
   1) providing the device of claim 1;
   2) wetting the teeth or the oral care layer of the device;
   3) placing the device over the teeth of a dental arch, and
   4) conforming the device to the teeth and surrounding tissue by manual pressure so that the oral care layer is in contact with at least the facial surface of the teeth.

132. The method of claim 131, wherein the oral care layer comprises a pressure-sensitive adhesive comprising at least one tooth whitening agent, at least one hydrophilic polymer, and at least one water-soluble plasticizer that is miscible with the hydrophilic polymer.

133. The method of claim 132, wherein the at least one hydrophilic polymer has a hydrophilicity as measured by water uptake greater than about 25%.

134. The method of claim 133, wherein the at least one hydrophilic polymer has a glass transition temperature T(g) or melting point T(m) higher than about 25° C. and lower than about 120° C.

135. The method of claim 134, wherein the oral care layer comprises at least one crosslinked or non-crosslinked polymer selected from the group consisting of 2-acrylamido-2-methyl-propanesulfonic acid; polyvinyl pyrrolidone; polyethylene oxide; acrylates; polyvinyl alcohol; and carboxylic acid polymers.

136. The method of claim 135, wherein the oral care layer comprises crosslinked or non-crosslinked 2-acrylamido-2-methyl-propanesulfonic acid.

137. The method of claim 135, wherein the oral care layer comprises crosslinked or non-crosslinked polyvinyl pyrrolidone.

138. The method of claim 131, wherein the oral care layer is a sustained release oral care layer.

139. The method of claim 137, wherein the oral care layer is a sustained release oral care layer.

140. The method of claim 139, wherein the sustained-release oral care layer releases the at least one tooth whitening agent at a rate of approximately 0.2 mg/cm$^2$-min to 1 mg/cm$^2$-min.

141. The method of claim 131, wherein the device is left on the teeth for about 15 minutes to about 4 hours.

142. The method of claim 131, wherein the device is left on the teeth for about 30 minutes to about 1 hour.

143. The method of claim 131, wherein the tooth whitening agent is selected from the group consisting of peroxides; metal chlorites; perborates; percarbonates; peroxyacids; and combinations thereof.

144. The method of claim 143, wherein the tooth whitening agent is a peroxide selected from the group consisting of hydrogen peroxide; calcium peroxide; carbamide peroxide; and mixtures thereof.

145. The method of claim 143, wherein the tooth whitening agent is a metal chlorite selected from the group consisting of calcium chlorite; barium chlorite; magnesium chlorite; lithium chlorite; sodium chlorite; and potassium chlorite; hypochlorite and chlorine dioxide.

146. The method of claim 131, wherein the concentration of tooth whitening agent in the oral care layer is about 0.01% to about 40%.

147. The method of claim 144, wherein the peroxide compound in the oral care layer provides an amount of peroxide equivalent to about 0.1% to about 20% of hydrogen peroxide.

148. The method of claim 144, wherein the peroxide compound in the oral care layer provides an amount of peroxide equivalent to about 0.5% to about 10% of hydrogen peroxide.

149. The method of claim 144, wherein the peroxide compound in the oral care layer provides an amount of peroxide equivalent to about 1% to about 7% of hydrogen peroxide.

150. The method of claim 144, wherein the peroxide compound in the oral care layer provides an amount of peroxide equivalent to about 6% of hydrogen peroxide.

151. The method of claim 144, wherein the amount of hydrogen peroxide in the oral care layer is from about 0.1% to about 30%.

152. The method of claim 144, wherein the amount of hydrogen peroxide in the oral care layer is from about 3% to about 20%.

153. The method of claim 144, wherein the amount of hydrogen peroxide in the oral care layer is from about 6% to about 10%.

154. A method of making the device of claim 1, comprising the steps of:
   1) providing a permanently deformable backing layer;
   2) attaching an anchor layer to the backing layer;
   3) extruding an oral care layer onto the anchor layer.

155. The method of claim 154, in which an aqueous solution of the oral care agent is printed onto the anchor layer prior to extruding the oral care layer onto the anchor layer.

156. The method of claim 154, further comprising placing a scrim on the anchor layer before extruding the oral care layer onto the anchor layer.

157. The method of claim 156, wherein the scrim comprises a non-woven polyolefin.

* * * * *

UNITED STATES PATENT AND TRADEMARK OFFICE
CERTIFICATE OF CORRECTION

PATENT NO. : 8,956,160 B2  Page 1 of 1
APPLICATION NO. : 10/187666
DATED : February 17, 2015
INVENTOR(S) : Michael P. Willison et al.

It is certified that error appears in the above-identified patent and that said Letters Patent is hereby corrected as shown below:

In the Claims

Column 30, Claim 1, Line 33:
    after "the surface of" delete "a"

Column 33, Claim 65, Line 27:
    after "at least" delete ","

Column 33, Claim 68, Line 40:
    delete "anti tartar" and insert -- anti-tartar --

Column 35, Claim 97, Line 51:
    delete "hydrates" and insert -- hydrated --

Signed and Sealed this
Twenty-seventh Day of October, 2015

Michelle K. Lee
*Director of the United States Patent and Trademark Office*